United States Patent
Liang

(10) Patent No.: US 11,395,804 B2
(45) Date of Patent: Jul. 26, 2022

(54) HYDROPHILIC NANOSTRUCTURED MEMBRANE ACTIVE ANTIMICROBIALS WITH HIGH ACTIVITY, SELECTIVITY AND BIODEGRADABILITY

(71) Applicant: Texas Tech University System, Lubbock, TX (US)

(72) Inventor: Hongjun Liang, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/264,890

(22) Filed: Feb. 1, 2019

(65) Prior Publication Data

US 2019/0231703 A1    Aug. 1, 2019

Related U.S. Application Data

(60) Provisional application No. 62/624,915, filed on Feb. 1, 2018.

(51) Int. Cl.

| | |
|---|---|
| A61K 9/51 | (2006.01) |
| A61P 31/04 | (2006.01) |
| B82Y 5/00 | (2011.01) |
| A61K 9/16 | (2006.01) |
| A61K 31/715 | (2006.01) |
| A61K 31/7004 | (2006.01) |
| A61K 9/00 | (2006.01) |
| A61K 9/20 | (2006.01) |
| A61K 9/68 | (2006.01) |
| A61K 9/10 | (2006.01) |

(52) U.S. Cl.
CPC ............ *A61K 9/51* (2013.01); *A61K 9/16* (2013.01); *A61K 31/7004* (2013.01); *A61K 31/715* (2013.01); *A61P 31/04* (2018.01); *B82Y 5/00* (2013.01); *A61K 9/0056* (2013.01); *A61K 9/0058* (2013.01); *A61K 9/0095* (2013.01); *A61K 9/10* (2013.01); *A61K 9/20* (2013.01)

(58) Field of Classification Search
None
See application file for complete search history.

(56) References Cited

U.S. PATENT DOCUMENTS

| | | | |
|---|---|---|---|
| 8,968,765 | B2 | 3/2015 | Chen et al. |
| 2011/0152512 | A1 | 6/2011 | Ryan |

OTHER PUBLICATIONS

Zheng (Doctoral Dissertation titled Development of Well-Defined Inorganic and Polymeric Nanostructures for Bio-Nanoengineering, issued in 2015).*

Jiang et al. (ACS Infect. Dis., 3, 676-687, 2017) Hydrophilic Phage-Mimicking Membrane Active Antimicrobials Reveal Nanostructure-Dependent Activity and Selectivity.*

Bhattacharya et al. (Prog. Polym. Sci. 29, 767-814, 2004) Grafting: a versatile means to modify polymers Techniques, factors and applications.*

Chakraborty, S., et al., "Ternary Nylon-3 copolymers as host-defense peptide mimics: Beyond hydrophobic and cationic subunits." J. Am. Chem. Soc. (2014), 136(41):14530-14535.

Chong, Y. K., et al., "Thiocarbonylthio end group removal from RAFT-synthesized polymers by radical-induced reduction." Macromolecules 2007, 40(13):4446-4455.

Hu, K, et al., "A critical evaluation of random copolymer mimesis of homogeneous antimicrobial peptides." Macromolecules (2013), 46(5):1908-1915.

Kuang, L. J., et al., "'Frozen' block copolymer nanomembranes with light-driven proton pumping performance." ACS Nano (2014), 8(1):537-545.

Lee, M. W., et al., "Interactions between membranes and "metaphilic" polypeptide architectures with diverse side-chain populations." ACS Nano (2017), 11(3):2858-2871.

Lienkamp, K., et al., "Antimicrobial Polymers Prepared by ROMP with Unprecedented Selectivity: A Molecular Construction Kit Approach." J Am Chem Soc (2008), 130(30):9836-9843.

Moad, G., et al., "Advances in RAFT polymerization: the synthesis of polymers with defined end-groups." Polymer 2005, 46(19):8458-8468.

Moad, G., et al., "Living radical polymerization by the RAFT process." Aust. J. Chem. 2005, 58(6):379-410.

Patten, T. E., et al., "Atom transfer radical polymerization and the synthesis of polymeric materials." Adv. Mater. (1998), 10(12):901-915.

Venkatesh, R., et al., "Novel brush copolymers via controlled radical polymerization." Macromol. Chem. Phys. 2004, 205 (16):2161-2168.

Zheng, Wan et al. "Environmentally Benign Nanoantibiotics with a Built-in Deactivation Switch Responsive to Natural Habitats" Biomacromolecules 2020, 21, 2187-2198.

* cited by examiner

*Primary Examiner* — Tigabu Kassa
(74) *Attorney, Agent, or Firm* — Edwin S. Flores; Daniel J. Chalker; Chalker Flores, LLP

(57) ABSTRACT

The present invention includes compositions and methods of making hydrophilic nanostructured antibiotics (i.e. nanoantibiotics), including nanoantibiotics that use environmentally degradable biomolecules as the backbone building blocks, wherein the backbone building blocks can include spherical backbones such as sucroses, cyclodextrins, glycogens, and phytoglycogen with different diameters, or rod-like backbone building blocks such as dextrins, amyloses, and celluloses with different lengths. These hydrophilic nanoantibiotics with well-defined sizes and shapes can selectively disrupt bacterial membranes (i.e., serve as membrane-active antimicrobials) while being benign to mammalian cells. Depending on the size and shape difference of the hydrophilic nanoantibiotics, they can also selectively kill one type of bacteria (e.g., gram-negative) over another type (e.g., gram-positive). The environmentally degradable nanoantibiotics will have built-in dismantling "switches" to dismantle and become antimicrobial inactive in responsive to environmental stimuli once released into natural habitat, hence greatly reducing the possibility of developing bacteria resistance.

6 Claims, 14 Drawing Sheets

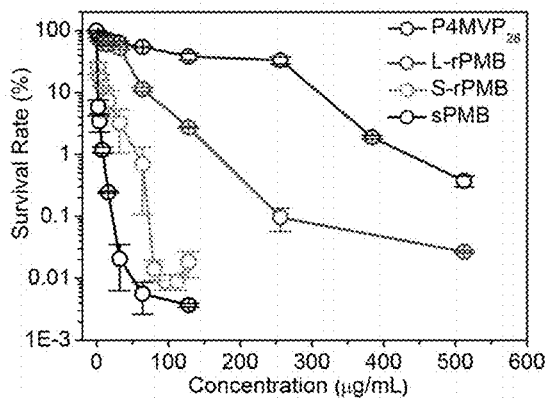
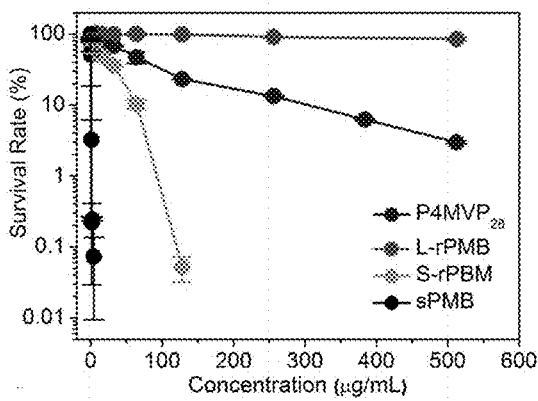
FIG. 3A
FIG. 3B
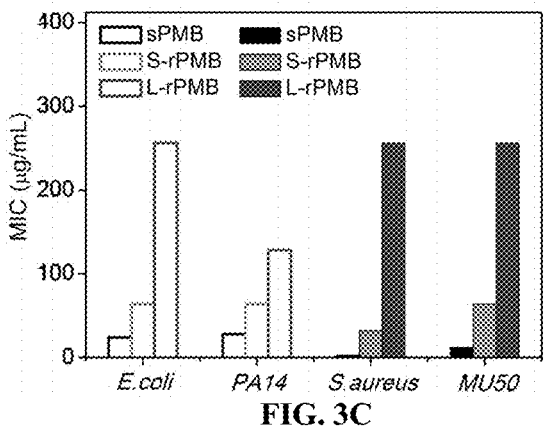
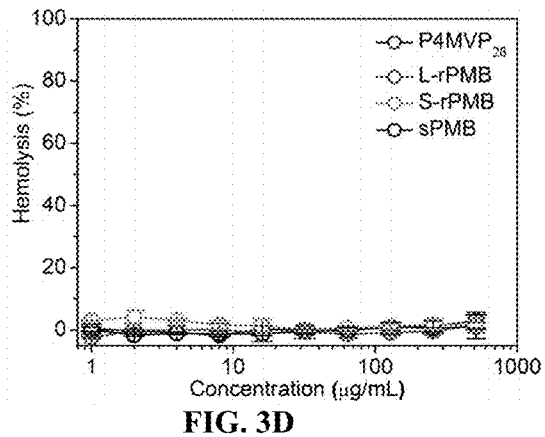
FIG. 3C
FIG. 3D
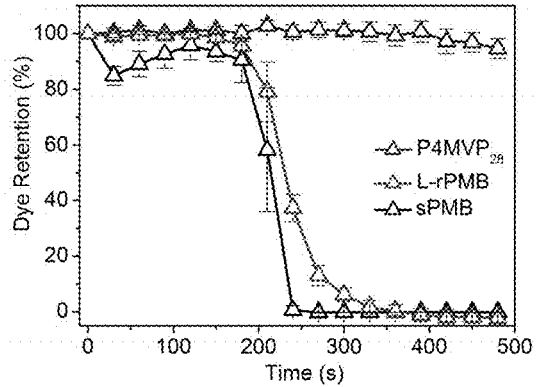
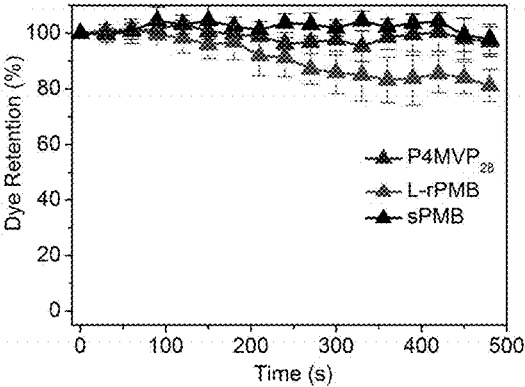
FIG. 4A
FIG. 4B
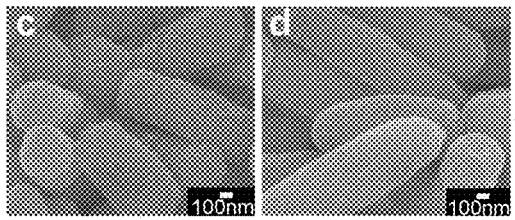
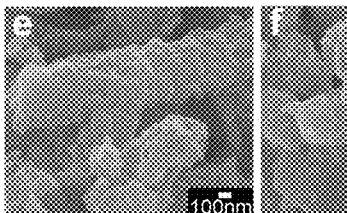
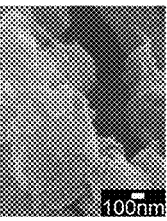
FIG. 4C    FIG. 4D    FIG. 4E    FIG. 4F

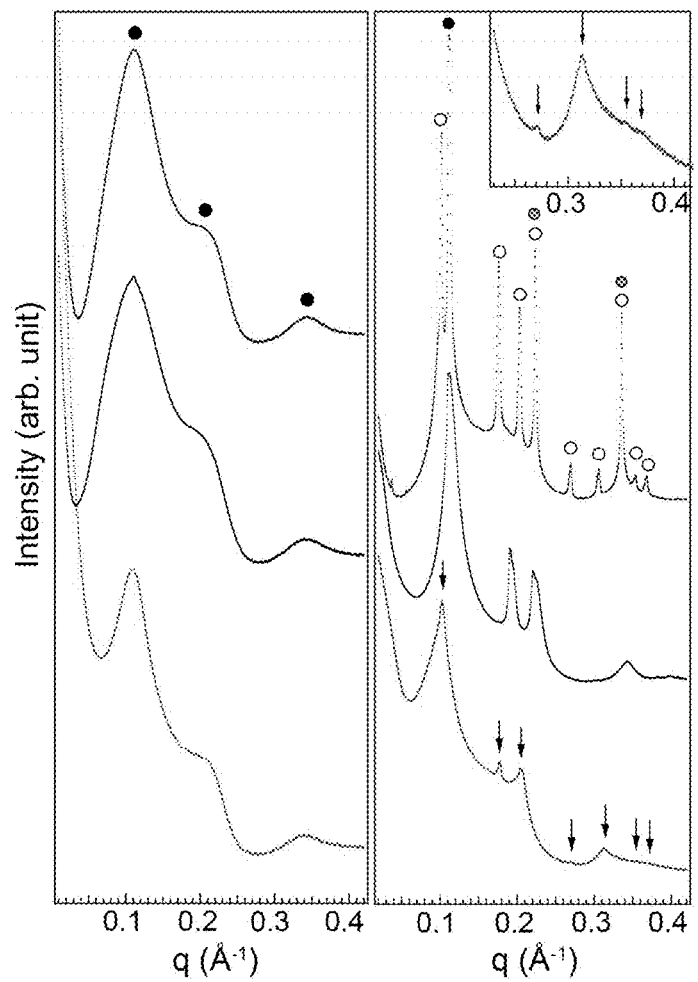
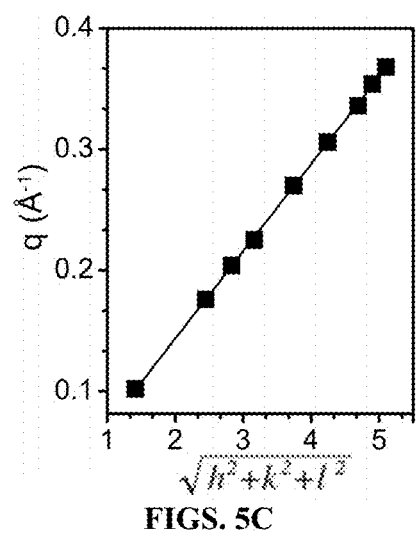
FIG. 5A   FIG. 5B
FIGS. 5C

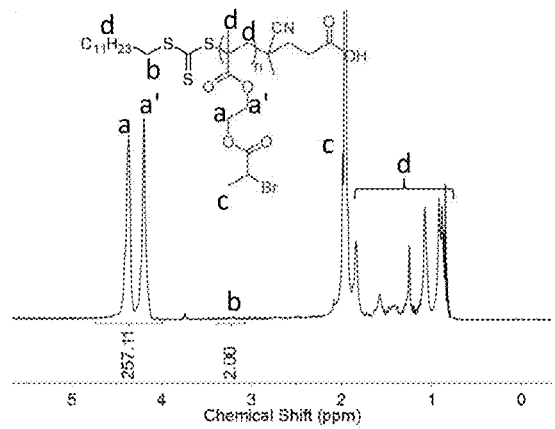
FIG. 15A
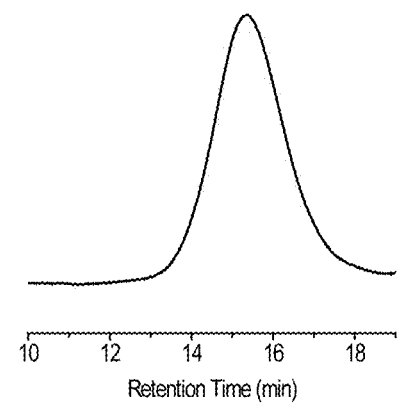
FIG. 15B
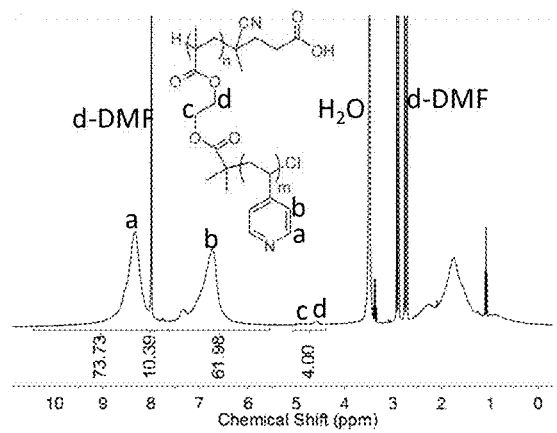
FIG. 15C
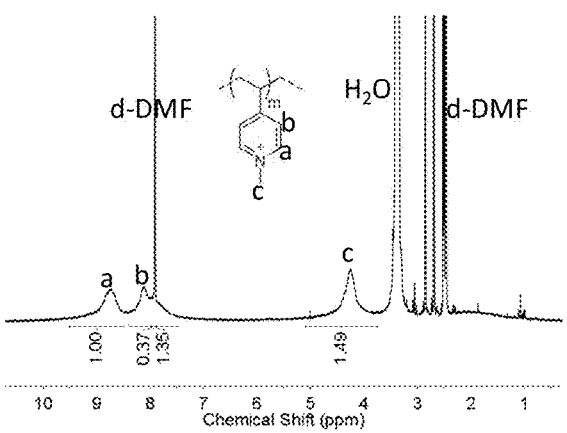
FIG. 15D
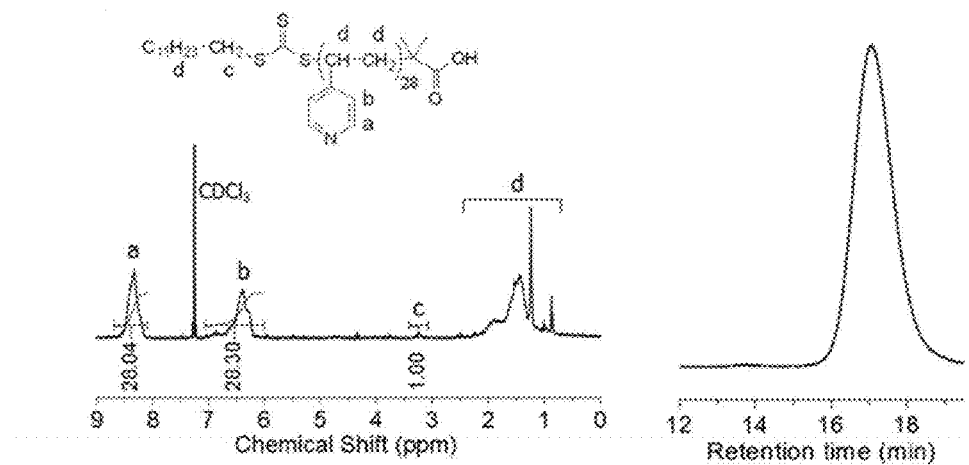
FIG. 16A  FIG. 16B

HYDROPHILIC NANOSTRUCTURED MEMBRANE ACTIVE ANTIMICROBIALS WITH HIGH ACTIVITY, SELECTIVITY AND BIODEGRADABILITY

STATEMENT OF FEDERALLY FUNDED RESEARCH

This invention was made with government support under DMR-1623241 and CBET-1623240 awarded by National Science Foundation. The government has certain rights in the invention.

CROSS-REFERENCE TO RELATED APPLICATIONS

None.

TECHNICAL FIELD OF THE INVENTION

The present invention relates in general to the field of new antibiotics that target bacterial infections including drug-resistant bacterial infections, and have a low risk of inducing bacterial resistance when released in the environment after use.

BACKGROUND OF THE INVENTION

Without limiting the scope of the invention, its background is described in connection with antibiotics.

Antimicrobial (host defense) peptides (AMPs) and synthetic mimics of AMPS (SMAMPs) have emerged as promising candidates for novel antibiotics. Cationic charge and amphiphilicity were identified as the two key antibiotic traits that help many AMPs disrupt bacterial membranes via synergistic hydrophobic and charge interactions. Because this mode of action damages bacterial membranes nonspecifically, the possibility of inducing resistance is greatly reduced. Nevertheless, direct use of AMPs is hindered by their expense, toxicity, and limited tissue distribution. Since the activity of AMPs relies on their overall physicochemical property rather than specific composition, much interest is put on developing SMAMPs, but a central dichotomy persists in that the hydrophobicity believed to be critical for their antimicrobial activity also causes their toxicity to mammalian cells. Numerous chemical variations have been tested in search of a delicate, yet unquantifiable cationic-hydrophobic balance, with recent progress aiming to unravel its implication. (Lee 2017, Hu 2013, Chakraborty 2014).

However, despite these developments a need remains for novel composition and methods that use novel chemistry to provide antimicrobial activity and that may also overcome existing antibiotic resistant strains of bacteria.

SUMMARY OF THE INVENTION

The present invention includes compositions and methods of making hydrophilic nanostructured antibiotics (i.e. nanoantibiotics), including nanoantibiotics that use environmentally biodegradable biomolecules as the backbone building blocks, wherein the backbone building blocks can include spherical backbones such as sucroses, cyclodextrins, glycogens, and phytoglycogen with different diameters, or rod-like backbone building blocks such as dextrins, amyloses, and celluloses with different lengths. These nanoantibiotics with well-defined sizes and shapes can selectively disrupt bacterial membranes (i.e., serve as membrane-active antimicrobials) while being benign to mammalian cells. Depending on the size and shape difference of the hydrophilic nanostructures, they can also selectively kill one type of bacteria (e.g., gram-negative) over another type (e.g., gram-positive).

In one embodiment, the present invention includes a method of making spherical polymer molecular brushes (PMBs) with specific structures and high hydrophilicity via controlled polymerization methods comprising:

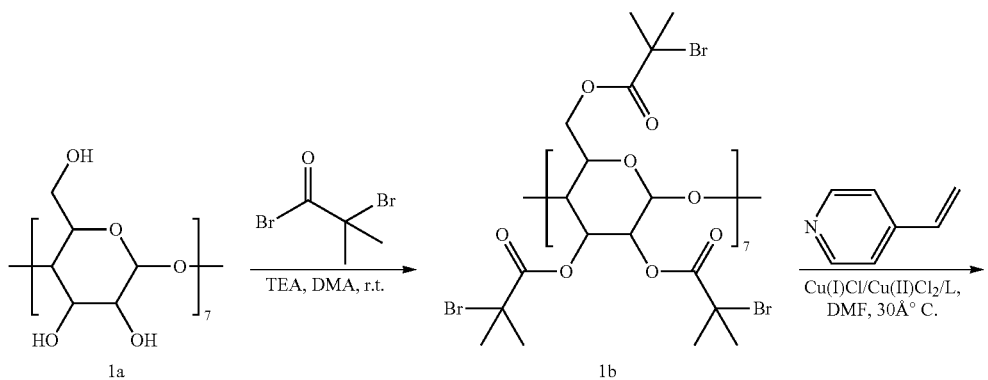

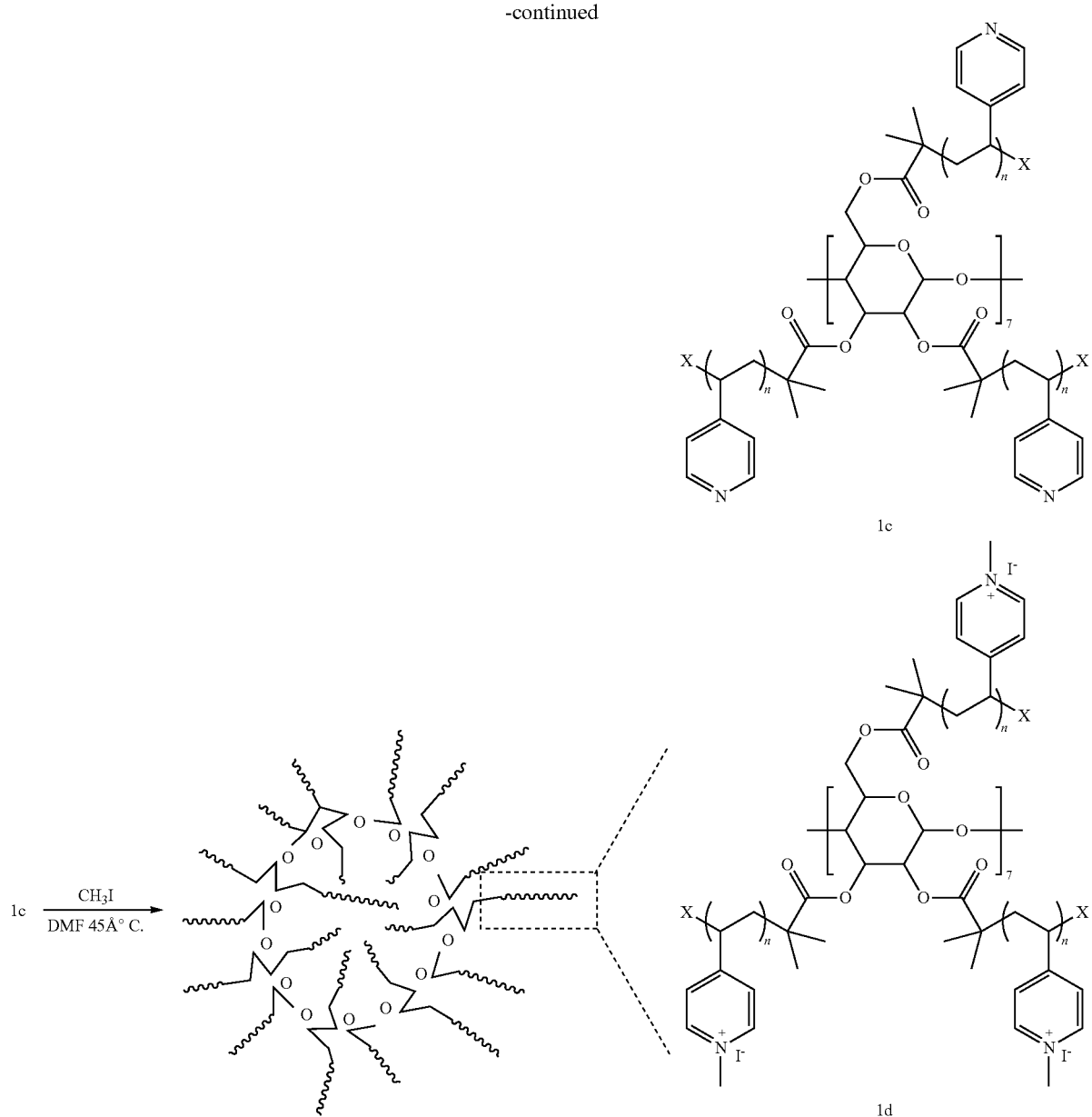

1c

1d

In one aspect, the length n is 1 to 20, 20 to 40, 40 to 60, 60 to 80, 80 to 100, or more than 100. In another aspect, X is selected from Cl or Br. In another aspect, a spherical backbone is selected from at least one of sucroses, cyclodextrins, glycogens, phytoglycogen or other environmentally degradable molecules. In another aspect, the hydrophilic polymer branches on the PMBs are either poly(4-vinyl-N-methylpyridine iodide) (P4MVP), poly(2-(trimethylamino)ethyl methacrylate) (PTMAEMA), or other polyelectrolytes including polyester and polypeptides. In another aspect, the PMB selectively disrupts bacterial membranes while not disrupting mammalian cell membranes. In another aspect, the PMB is environmentally biodegradable. In another aspect, the PMB has antimicrobial activity while in use in an animal but is dismantled into antimicrobially inactive pieces when released into a natural habitat. In another aspect, the PMB is a nanostructure that is either a nanorod or a nanosphere. In another aspect, the PMB consists essentially of a structure shown in FIG. 1A or FIG. 1B. In another aspect, the PMB is formulated in a pharmaceutically acceptable carrier in an amount effective to reduce or eliminate a bacterial infection.

In another embodiment, the present invention includes a method of making rod-like polymer molecular brushes (PMBs) with well-defined structures and high hydrophilicity via controlled/"living" polymerization methods comprising:

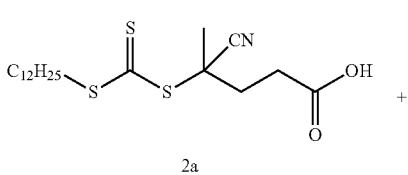

2a

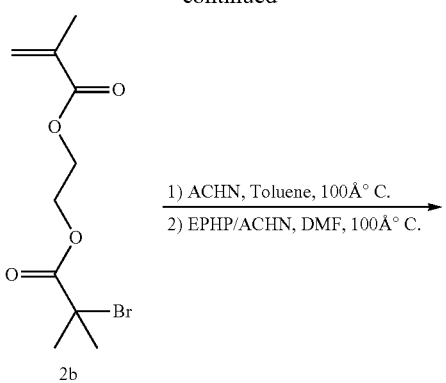

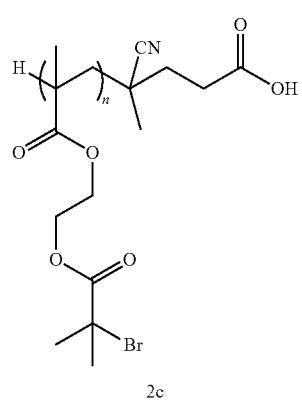

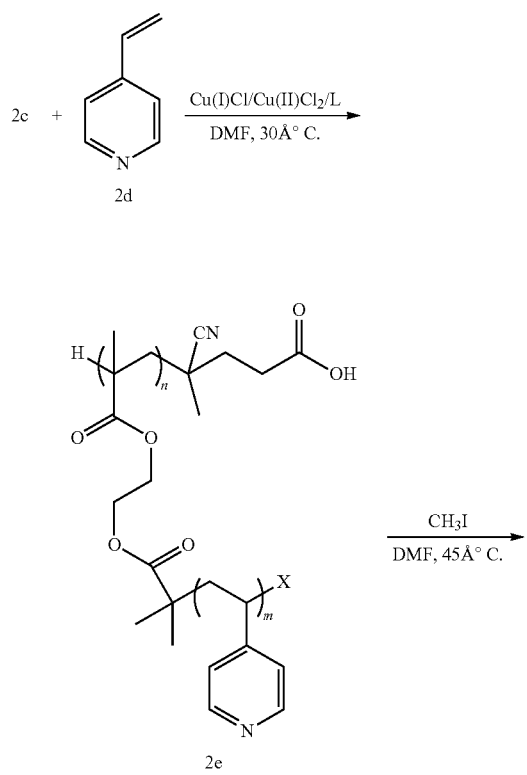

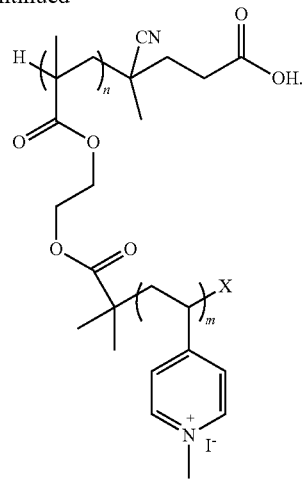

In one aspect, m is 1 to 100, 100 to 300, 300 to 500, or above 500. In another aspect, the n is 1 to 20, 20 to 40, 40 to 60, 60 to 80, 80 to 100, or more than 100. In another aspect, the X is selected from Cl or Br. In another aspect, a rod-like backbone is selected from at least one of dextrins, amyloses, chitosan, celluloses, or other environmentally biodegradable polymers. In another aspect, the hydrophilic polymer brushes are either poly(4-vinyl-N-methylpyridine iodide) (P4MVP), poly(2-(trimethylamino)ethyl methacrylate) (PTMAEMA), or other polyelectrolytes including polyester and polypeptides.

In another embodiment, the present invention includes an antimicrobial agent comprising: a rod-like polymer molecular brush (PMB) with high hydrophilicity comprising the formula:

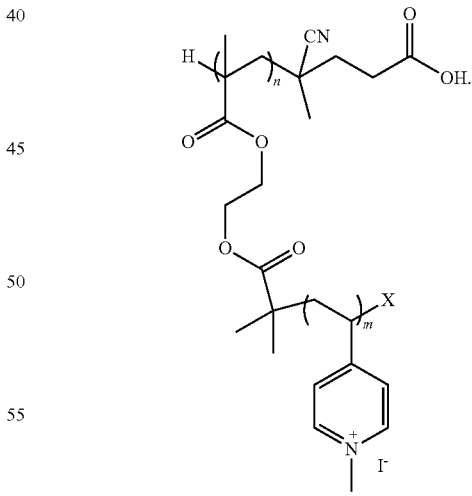

In one aspect, X is selected from Cl or Br. In another aspect, the antimicrobial agent further comprises one or more pharmaceutically acceptable carriers, one or more additional biologically active substances, and wherein the composition is adapted for the treatment of microbial infections. In another aspect, the antimicrobial agent further comprises one or more pharmaceutically acceptable excipients that form a liquid suspension, chewable composition, orally disintegrating tablet, sublingual, a modified release orally disintegrating tablet, or a swallowed tablet composition. In another aspect, a rod-like backbone is selected from at least one of dextrins, amyloses, chitosan, celluloses, or other environmentally degradable polymers. In another aspect, the PMB selectively disrupts bacterial membranes while not disrupting mammalian cell membranes. In another aspect, the PMB is environmentally biodegradable. In another aspect, the PMB has antimicrobial activity while in an animal but is dismantled into antimicrobially inactive pieces when released into a natural habitat. In another aspect, the PMB is a nanostructure that is either a nanorod or a nanosphere. In another aspect, the PMB consists essentially of a structure shown in FIG. 1A or FIG. 1B. In another aspect, the PMB is formulated in a pharmaceutically acceptable carrier in an amount effective to reduce or eliminate a bacterial infection.

In another embodiment, the present invention includes an antimicrobial agent comprising: a spherical polymer molecular brush (PMB) with high hydrophilicity comprising the formula:

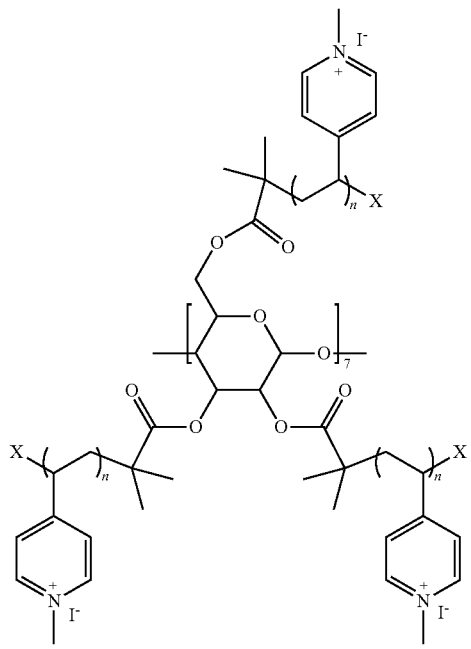

In one aspect, the X is selected from Cl or Br. In another aspect, a spherical backbone for the PMB is selected from at least one of sucroses, cyclodextrins, glycogens, phytoglycogen or other environmentally degradable molecules. In another aspect, the antimicrobial agent further comprises one or more pharmaceutically acceptable carriers, one or more additional biologically active substances, and wherein the composition is adapted for the treatment of microbial infections. In another aspect, the antimicrobial agent further comprises one or more pharmaceutically acceptable excipients that form a liquid suspension, chewable composition, orally disintegrating tablet, sublingual, a modified release orally disintegrating tablet, or a swallowed tablet composition. In another aspect, the PMB selectively disrupts bacterial membranes while not disrupting mammalian cell membranes. In another aspect, the PMB is environmentally biodegradable. In another aspect, the PMB has antimicrobial activity while in an animal but is dismantled into antimi- crobially inactive pieces when released into a natural habitat. In another aspect, the PMB is a nanostructure that is either a nanorod or a nanosphere. In another aspect, the PMB consists essentially of a structure shown in FIG. 1A or FIG. 1B. In another aspect, the PMB is formulated in a pharmaceutically acceptable carrier in an amount effective to reduce or eliminate a bacterial infection.

BRIEF DESCRIPTION OF THE DRAWINGS

For a more complete understanding of the features and advantages of the present invention, reference is now made to the detailed description of the invention along with the accompanying figures and in which:

FIGS. 3A to 3D shows the nanostructure-dependent antimicrobial selectivity and low toxicity of hydrophilic PMBs. (FIG. 3A, FIG. 3B) Bacteria killing assays of PMBs and P4MVP$_{28}$ against E. coli and S. aureus, respectively. (FIG. 3C) Bacteria inhibitory assays of the PMBs. (FIG. 3D) Hemolysis assays of PMBs and P4MVP$_{28}$. All data are represented as average±SD.

FIGS. 4A to 4F show that selective membrane disruption depends on both lipid composition and the polymer nanostructures. Time-lapse dye leakage from GUVs that mimic E. coli (FIG. 4A) and mammalian cells (FIG. 4B) after interacting with PMBs and P4MVP$_{28}$ reveals different membrane disruption. All data are represented as average±SD. The correlation between membrane disruption and the membrane active antimicrobial activity is further demonstrated by SEM pictures of E. coli control (FIG. 4C) and that incubated with P4MVP$_{28}$ (FIG. 4D), L-rPMB (FIG. 4E) and sPMBs (FIG. 4F), respectively.

FIGS. 5A to 5D show membrane remodeling by hydrophilic polymer antimicrobials depends on both lipid composition and the polymer nanostructures. Synchrotron Small-angle X-ray scattering (SAXS) of mammalian cell— (FIG. 5A) and E. coli-mimicking liposomes (FIG. 5B) after interacting with L-rPMB (red), sPMB (black), and P4MVP$_{28}$ (blue), respectively, show different structures. Inset in (FIG. 5B) is a blown-out view (0.23-0.42 Å$^{-1}$) of the SAXS of E. coli-mimicking liposomes remodeled by the L-rPMB. The SAXS of E. coli-mimicking liposomes remodeled by P4MVP$_{28}$ fits the scatterings from a bicontinuous cubic (Im3m) phase (FIG. 5C), where h, k, and l are the Miller indices, while that remodeled by PMBs (L-rPMB was shown as an example) fits a 2D hexagonal lattice (FIG. 5D).

(FIG. 6A) Fourier reconstructed 3D electron density map of *E. coli*-mimicking membrane incubated with L-rPMB reveals the formation of 2D hexagonally packed pores. The color scale bar of electron density ($\rho$) is shown at the top, and x/a, y/a represent perpendicular axes along the membrane plane normalized by the lattice parameter. (FIG. 6B) The 1D electron density profile along the unit cell x-axis further confirms that each PMB ($\rho=0.74$ e/Å$^3$) sits in the center of individual pores and is surrounded by a rim ($\rho=0.55$ e/Å$^3$) of lipid headgroups that are closely associated with the P4MVP branches of each PMB, and the pores organize themselves into an inverted 2D hexagonal membrane phase ($H_{II}$) as schematically shown in (FIG. 6C) (blue: P4MVP branches; red: PMB core; green: lipid tails; yellow and magenta: the headgroups of DOPG and DOPE, respectively).

FIGS. 15A to 15D show the successful synthesis of the short rod-like S-rPMB, PBIEM$_{64}$-g-P4MVP$_{31}$.

FIG. 16A to 16C show the linear-chain P4MVP$_{28}$ control prepared via RAFT polymerization.

DETAILED DESCRIPTION OF THE INVENTION

Figure 1A:
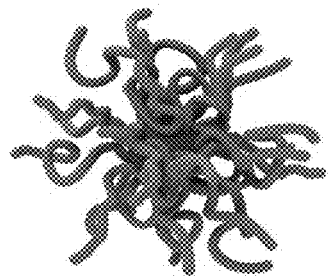
FIGS. 1A to 1D show the novel molecules synthesized, which are: spherical (a) and rod-like (b) polymer molecular brushes (PMBs) that mimic two basic structural motifs of bacteriophages. Their chemical structures are shown in (FIG. 1C) and (FIG. 1D), with blue chains representing P4MVP, and red cores representing β-CD (in FIG. 1A, FIG. 1C) and PBIEM (in FIG. 1B, FIG. 1D), respectively.
Figure 1C:
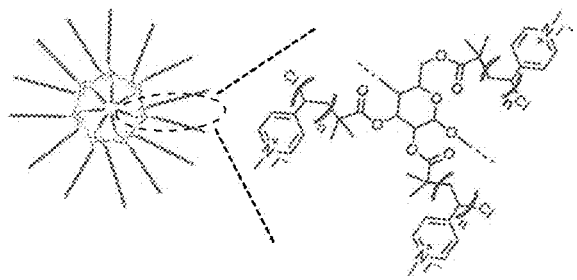
Figure 1B:
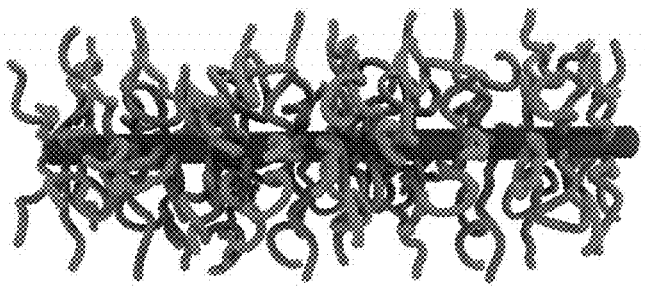
Figure 1D:
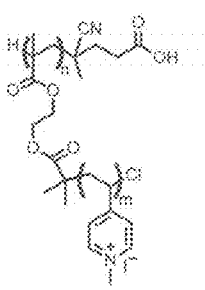

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Abbreviations. MAA, membrane-active antimicrobial; AMP, antimicrobial peptide; SMAMP, synthetic mimics of antimicrobial peptide; ATRP, atom transfer radical polymerization; RAFT, reversible addition-fragmentation chain transfer; PBIEM, poly(2-(bromoisobutyryl) ethyl methacrylate); β-CD, β-cyclodextrin; PMB, polymer molecular brush; sPMB, spherical polymer molecular brush; L-rPMB, long rod-like polymer molecular brush; S-rPMB, short rod-like polymer molecular brush; P4VP, poly(4-vinylpyridine); P4MVP, poly(4-vinyl-N-methylpyridine iodide); P4BVP, poly(4-vinyl-N-butylpyridine iodide); P4HVP, poly(4-vinyl-N-hexylpyridine iodide); P4DVP, poly(4-vinyl-N-dodecylpyridine iodide); GUV, giant unilamellar vesicle; DOPG, 1,2-dioleoyl-sn-glycero-3-phospho-(1'-rac-glycerol); DOPC, 1,2-dioleoyl-sn-glycero-3-phosphocholine; DOPE, 1,2-dioleoyl-sn-glycero-3-phosphoethanolamine; RBC, human red blood cell; MBC, minimum bactericidal concentration; MIC, minimum bacteria inhibitory concentration; SAXS, small angle x-ray scattering; GPC, gel permeation chromatography; NMR, nuclear magnetic resonance spectroscopy; FTIR, Fourier transform infrared spectroscopy; SEM, scanning electron microscopy; TEM, transmission electron microscopy; AFM, atomic force microscopy.

The present invention teaches the development of novel hydrophilic nanoantibiotics that disrupt microbial membranes by inducing a topological transition of the membranes to form pores without breaching the hydrophobic membrane interior. Hydrophobicity is no longer an indispensable antibiotic trait for the design of these nanoantibiotics. This is in contrast to other AMPs or SMAMPs under development that often incorporate hydrophobic moieties in their design, and constantly search for a delicate hydrophobic-cationic balance to trade antimicrobial activity with toxicity.

This invention teaches a general strategy to transform various hydrophilic polymers that have excellent biocompatibility but poor antimicrobial activity into potent nanoantibiotics by assembling them into nanostructures, and teaches that the nanostructure-associated multivalent interaction is the key driving force for this transformation.

This invention teaches that the hydrophilic nanoantibiotics recognize lipid composition difference between mammalian and microbial membranes to selectively disrupt the latter, because only the microbial membranes laden with negative-intrinsic-curvature lipids are able to overcome the bending energy cost to wrap around the nanoantibiotics to form membrane pores.

This invention also teaches that the hydrophilic nanoantibiotics recognize the cell wall difference between Gram− and Gram+ bacteria, because the thick ananoporous peptidoglycan layer of Gram+ bacteria act as a selective filter for the nanoantibiotics to gain access to the bacterial membrane, while the thin peptidoglycan layer sandwiched between the outer and inner membranes of Gram− bacteria only plays a limited role on restricting PMB actions.

The present invention teaches the development of novel nanoantibiotics using environmentally degradable biomolecules as the backbone building blocks. These biomolecules include spherical backbones such as sucroses, cyclodextrins, glycogens, and phytoglycogen with different diameters, or rod-like backbones such as dextrins, amyloses, and celluloses with different length. Many of these biomolecules can't be easily degraded in human body, but can be degraded by various enzymes from living organisms present in the environment.

Thus, these hydrophilic nanostructures with well-defined sizes and shapes can selectively disrupt bacterial membranes (i.e., serve as membrane-active antimicrobials) while being benign to mammalian cells. Depending on the size and shape difference of the hydrophilic nanostructures, they can also selectively kill one type of bacteria (e.g., gram-negative) over another type (e.g., gram-positive).

This invention teaches the development of environmentally degradable nanoantibiotics with triple selectivity, i.e. besides the selectivity between bacteria and human cells (i.e. the $1^{st}$ selectivity), and that between different bacteria (i.e. the $2^{nd}$ selectivity), the nanoantibiotics can be made to possess the $3^{rd}$ selectivity between bacteria in human body and that in natural habitats. In contrast to conventional antibiotics that accumulate in soils and waterways, the environmentally degradable nanoantibiotics will have built-in dismantling "switches" to dismantle and become antimicrobial inactive in responsive to environmental stimuli once released into natural habitat, hence greatly reducing the possibility of developing bacteria resistance.

The present invention includes the development of nano-antibiotics with high activity and selectivity and low toxicity. Once the nanoantibiotics finish their job and are released into natural habitats, they will not accumulate at increasing concentrations that would otherwise encourage bacteria to eventually develop resistance.

The present invention includes hydrophilic and biodegradable nanoantibiotics as a new family of membrane active antimicrobials. Because of their hydrophilic nature, well-defined nanostructures, and biodegradability, they show high activity on bacteria and low toxicity on mammalian cells. They also show size- and shape dependent selectivity on different families of bacteria. Their membrane active mode of action and their environmental degradability ensure their efficacy on even antibiotic-resistant bacteria while in use, and low risk of inducing bacterial resistance when released in the environment after use. In particular, this invention helped solve one or more of the following problems. (1) Existing antibiotic resistant bacteria infections. The nanoantibiotics are membrane active. Bacterial resistance to the membrane active antimicrobial has not emerged yet. (2) prevents future development of resistant bacteria species. Unlike conventional antibiotics, the nanoantibiotics are environmentally biodegradable. They will not accumulate in natural habitats to encourage bacteria to develop resistance. (3) General toxicity of membrane active antimicrobials. Unlike the conventional membrane active antimicrobials that are amphiphilic and often have unacceptable toxicity levels, the hydrophilic nanoantibiotics keep their high antimicrobial activity while remaining non-toxic. (4) General low selectivity of membrane active antimicrobials. Unlike the conventional membrane active antimicrobials that often have low selectivity between mammalian cells and bacterial cells, or between different families of bacteria, the nanoantibiotics are found to have high selectivity among both categories depending on their sizes and shapes. It is a promising approach to develop personalized antibiotics with target specificity. (5) High production cost and high environmental risk on waste disposal. Most conventional antibiotics are produced through expensive multi-step synthesis and purification with hazardous waste generation. The nanoantibiotics are produced using abundant biorenewable resources and green chemistry that are environmentally benign.

The advantages of the present invention include: (1) the nanoantibiotics target and disrupt bacterial membranes instead of specific biosynthetic pathways. As such, it is difficult for bacteria to develop resistance; (2) the nanoantibiotics are biodegradable by various enzymes present in natural habitats. As such, they don't accumulate at increasing concentrations when release into environment, which would otherwise encourage bacteria to eventually develop resistance; (3) the nanoantibiotics are hydrophilic. They don't disrupt bacterial membrane via hydrophobic interactions like other reported membrane active antimicrobials. Instead, the nanostructures give rise to their structure-associated multivalent interactions to remodel bacterial membranes. This membrane remodeling only occurs in microbial membranes because only microbial membranes have high concentration of negative-curvature lipids. The negative curvature lipids are needed to offset the energy cost to wrap the membrane around these nanostructures to form pores. In contrast, mammalian cells have high concentration of zero-curvature lipids that don't support this membrane remodeling; (4) The selectivity between bacteria and mammalian cells is realized through the nanostructure-dependent multivalent interactions that recognize the membrane lipid difference between bacteria and mammalian cells; the selectivity between gram+ and gram− bacteria is realized through the nanostructure-dependent disruption and penetration of bacterial cell walls because the two families of bacteria have different membrane structures: the gram− bacteria have an outer membrane that will interact with nanoantibiotics upon contact, while the gram+ bacteria have a thick peptidoglycan encapsulation outside their plasma membranes. The thickness and "mesh" size of this peptidoglycan encapsulation layer define the accessibility of nanoantibiotics to disrupt the bacterial membranes with a size- and shape-dependent activity; and/or (5) The present inventors used green chemistry (i.e., ionic liquid based synthesis) to modify both spherical and rod-shaped natural biopolymers to grow polymer brushes in a one-step reaction. The hydrophilic polymer brushes can be polypeptides, polyacrylates, or polyesters that are biodegradable, and they are not antibiotic active by themselves. When assembled covalently to form nanostructures, they become antibiotic active with a size- and shape-dependent activity and selectivity. The production and waste disposal is environmental friendly and easy for scale-up production.

The present invention used a different approach to develop membrane-active antimicrobials (MAAs) by designing spherical and rod-like polymer molecular brushes (PMBs) that mimic the two basic structural motifs of bacteriophages (FIGS. 1A to 1D). The novel compositions mimic the nanoscale viral structural features that give rise to their multivalent interactions on remodeling bacterial membranes. Phages use proteinaceous devices that are first and foremost recognized by their unique nanostructures to selectively attack bacteria and gain entrance or egress. Some phages, such as the spherical Φ6 and Φ13, penetrate bacterial membranes directly; others use protein passages, such as the rod-like tail tube of bacteriophage T4, or membrane pores self-assembled by holins and pinholins. Although the size- and shape-dependency of nanoparticle uptake by mammalian cells is well known, and the disruptive activity of various nanostructures on bacterial cells is known, most of these antibiotic nanostructures fit in the wisdom of balancing cationic charge with hydrophobicity, and the role of nanostructure itself on regulating the antimicrobial activity and selectivity has not been examined.

To reveal the antibiotic role of nanostructures, the present inventors designed model PMBs with different well-defined geometries consisting of multiple identical copies of a densely packed hydrophilic polymer branch that by itself has low antimicrobial activity, reminiscent of the viral structural motifs comprised of multiple copies of protein subunits. This design eliminates hydrophobic interactions that indistinctively disrupt both bacterial and mammalian membranes, hence bypassing the experimentation to seek an elusive cationic-hydrophobic balance.

Figure 16C:
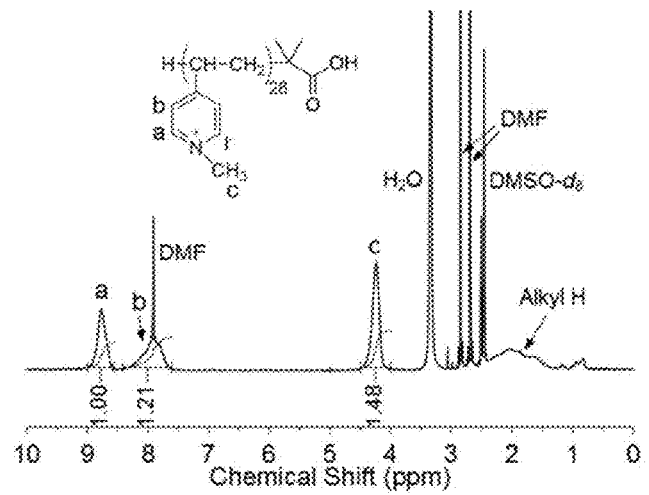

Reaction details to prepare spherical and rod-like model PMBs with well-defined geometries via controlled/"living" free radical polymerization[53-54] are discussed in detail herein below. Briefly, the inventors prepared spherical PMBs by converting the β-cyclodextrin (β-CD) into a 21-arm macroinitiator for atom transfer radical polymerization (ATRP) of poly(4-vinylpyridine) (P4VP) branches, which were then quaternized by methyl iodide to become hydrophilic and cationic poly(4-vinyl-N-methylpyridine iodide) (P4MVP). The rod-like PMBs were prepared by first synthesizing poly(2-(bromoisobutyryl) ethyl methacrylate) (PBIEM) via reversible addition-fragmentation chain transfer (RAFT) polymerization. After its trithiocarbonate moiety was removed, the PBIEM backbone was used as an ATRP macroinitiator to grow P4MVP branches in a similar way as mentioned above. The inventors used gel permeation chromatography (GPC), nuclear magnetic resonance (NMR), and Fourier transform infrared (FTIR) spectroscopy together with brush cleavage experiments to determine the brush size, graft density, and the degree of quaternization, and confirmed the successful synthesis of three well-defined model PMBs: a spherical β-CD-g-P4MVP$_{28}$ (referred as "sPMB"), a short rod-like PBIEM$_{64}$-g-P4MVP$_{31}$ ("S-rPMB"), and a long rod-like PBIEM$_{254}$-g-P4MVP$_{29}$ ("L-rPMB") (see also FIGS. 11-15). Their molecular weight is 149, 507, and 1,886 kD, respectively, which is 2-3 orders of magnitude higher than most previously studied SMAMPs, but on a par with the protein devices of many phages. The inventors calculated the diameter (d) and length (l) of the PMBs based on the contour length of P4MVP and PBIEM, respectively, and the diameter of the β-CD core (1.5 nm). Atomic force microscopy (AFM) studies on PMBs confirmed that both their backbones and side-chains take an extended all-trans conformation, and the respective contour lengths match well with their actual sizes measured by AFM. The spherical sPMB has d~8.5 nm, while the rod-shaped S-rPMB and L-rPMB have a similar d (~7 nm) but increasing l from ~18 to ~70 nm. These physical dimensions are comparable to the structural motifs of phages, such as the tail tube of bacteriophage T4 (l~94 nm; d~9.6 nm). The inventors used standard bacteria killing and inhibitory assays to study their antibiotic activities against the Gram− E. coli and Gram+ S. aureus, and compared that with the linear-chain P4MVP controls either cleaved from the PMBs or synthesized separately (FIGS. 16A-C). The inventors also tested their antimicrobial potency on clinical multidrug resistant bacterial strains, Gram− PA14 (i.e. tobramycin and gentamycin resistant P. aeruginosa) and Gram+ MU50 (i.e. methicillin, oxacillin, and vancomycin resistant S. aureus), and their toxicity on human red blood cells (RBCs) by hemolysis assay to obtain HC$_{50}$[20-26] and hemagglutination assay.

Figure 2:
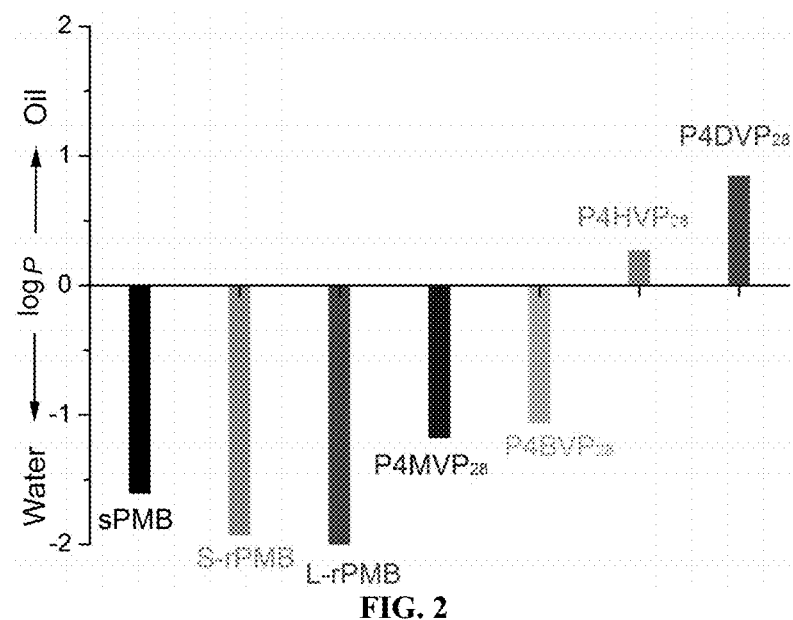
FIG. 2 is a graph that shows the hydrophilicity of nanostructured PMBs and linear-chain P4VP$_{28}$ quaternized by different alkyl iodides are compared by their partition coefficient at the oil/water interface. All nanostructured PMBs remain highly hydrophilic, even more so than individual P4MVP$_{28}$. In contrast, P4VP$_{28}$ quaternized by alkyl iodides of increasing alkyl chain length (butyl—P4BVP$_{28}$; hexyl—P4HVP$_{28}$; and dodecyl—P4DVP$_{28}$) becomes increasingly hydrophobic. The moderately hydrophobic P4HVP$_{28}$ is antimicrobial active but very hemolytic (see also FIGS. 17A-17B).

The Hydrophilic Phage-Mimicking PMBs Exhibit Nanostructure-Dependent Antimicrobial Activity and Double Selectivity. Hydrophilic and cationic linear-chain polymers are weak antimicrobials with low hemolytic activity.[20-27] Increasing hydrophobicity will improve their antimicrobial activity, albeit at the cost of deteriorated hemocompatibility because the same hydrophobic interactions that disrupt bacterial membranes also damage mammalian cells.[14-18] This old dilemma is well displayed in a series of linear-chain P4VP$_{28}$ branches quaternized by alkyl iodides of different chain length (FIGS. 17A-B): the cationic and hydrophilic P4MVP$_{28}$ (FIG. 2) is not hemolytic but a weak antimicrobial, comparing to the cationic and hydrophobic P4HVP$_{28}$ that is the most antibiotic but also very hemolytic.

Interestingly, when individual P4MVP$_{28}$ branches are covalently assembled to form the nanostructured PMBs, even though the hydrophilicity as represented by their water/oil partition coefficient (P) is further improved (FIG. 2), some fundamental transition occurs and amphiphilicity is no longer a required antibiotic trait. All PMBs become antimicrobials against the Gram− E. coli with nanostructure-dependent activity (FIG. 3A). The minimum bactericidal concentration (MBC), which is the dosage at which >99.9% bacteria are killed, is continuously reduced from L-rPMB to S-rPMB and sPMB, whereas the linear-chain P4MVP$_{28}$ doesn't show MBC up to 512 μg/ml that we tested. A similar nanostructure-dependent antimicrobial activity is also observed against the Gram+ S. aureus (FIG. 3B): the MBC of nanostructured PMBs is reduced sharply from L-rPMB to S-rPMB and sPMB, while the linear-chain P4MVP$_{28}$ still doesn't show MBC up to 512 μg/ml. Notably, the L-rPMB that has a similar d as the sPMB but a much larger aspect ratio (i.e. 10 vs 1) shows no bactericidal activity against S. aureus. Apparently, assembly of individual P4MVP$_{28}$ branches into nanostructured PMBs transform their antimicrobial activity, and the size and shape of the nanostructures further help PMBs define their activity and selectivity against different families of bacteria.

TABLE 1

A summary of the biological activity.

| | MBC (µg/ml) | | | | MIC (µg/ml) | | | | HC$_{50}$ |
| --- | --- | --- | --- | --- | --- | --- | --- | --- | --- |
| | E.C.[a] | PA14 | S.A.[b] | MU50 | E.C. | PA14 | S.A. | MU50 | RBC |
| P4MVP$_{28}$ | no[c] | 512 | no | 256 | no | no | 24 | 128 | no |
| L-rPMB | 256 | 4 | no | 512 | 256 | 128 | 256 | 256 | no |
| S-rPMB | 80 | 2 | 128 | 128 | 64 | 64 | 32 | 64 | no |
| sPMB | 32 | 2 | 4 | 32 | 24 | 28 | 3 | 12 | no |

[a]E. coli.
[b]S. aureus.
[c]not obtained up to 512 µg/ml.

To test the broad implication of this concept, we included two clinical multidrug resistant bacterial strains, i.e. the Gram– PA14 and Gram+ MU50, respectively, and also measured the minimum bacteria inhibitory concentration (MIC). The results of all biological tests are summarized in Table 1. The PMBs show superior MBC against PA14, and similar nanostructure-dependent MBC against MU50. As for MIC, except for the linear-chain P4MVP$_{28}$ that shows MIC against the Gram+ but not the Gram– bacterial strains, all PMBs exhibit similar nanostructure-dependent MIC for each bacterial strain (FIG. 3C): the sPMB is the most active with the lowest MIC; when the shape of sPMB is elongated to become S-rPMB and L-rPMB that have a similar d but increasing l, the MIC continuously increases. The MBC and MIC of sPMB are among some of the best reported numbers of AMPs and SMAMPs,[8-31] e.g., its MBC and MIC against S. aureus is 4 and 3 µg/ml, respectively, equivalent to 0.027 and 0.02 µM.

Figure 18:
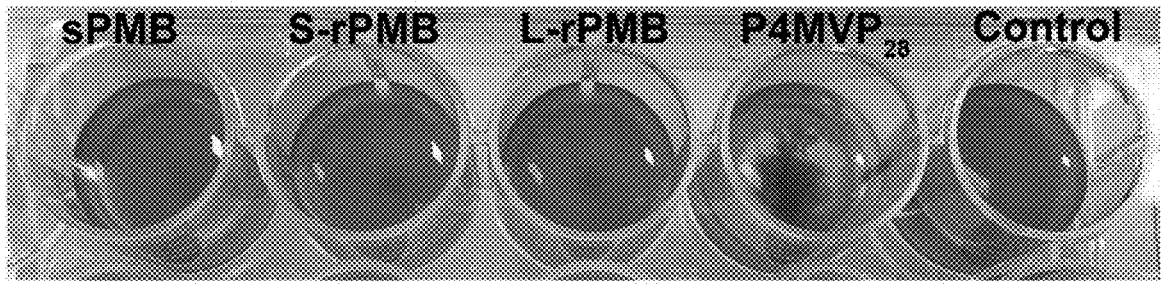
FIG. 18 shows a comparison of the hemagglutination activity between nanostructured PMBs and linear-chain P4MVP$_{28}$.
Figure 19A:
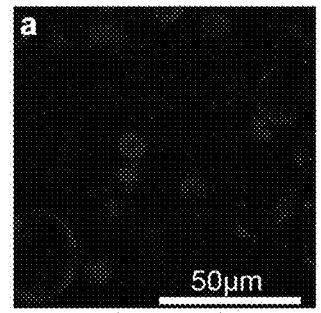
FIGS. 19A to 19L are confocal microscopy images that show no dye leakage from mammalian cell-mimicking GUVs when interacting with PMBs and P4MVP$_{28}$ (scale bar: 50 μm).
Figure 19B:
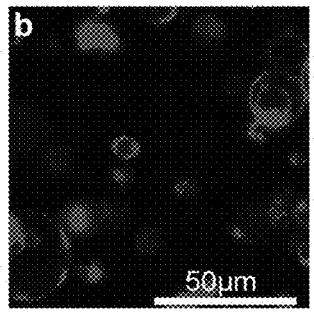
Figure 19C:
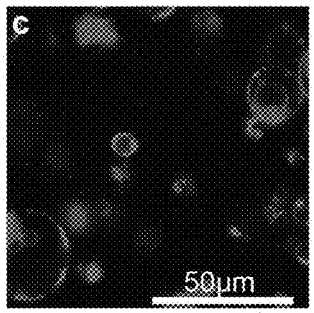
Figure 19D:
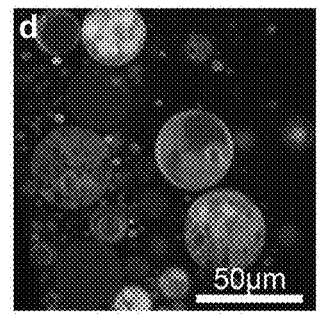
Figure 19E:
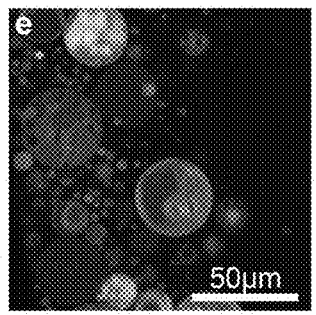
Figure 19F:
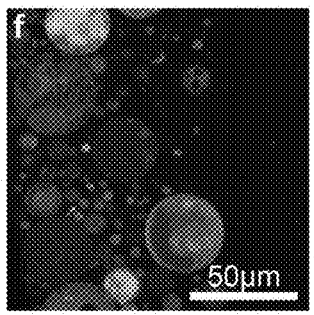
Figure 19G:
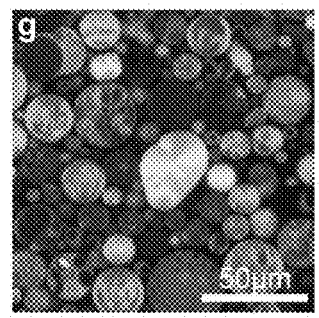
Figure 19H:
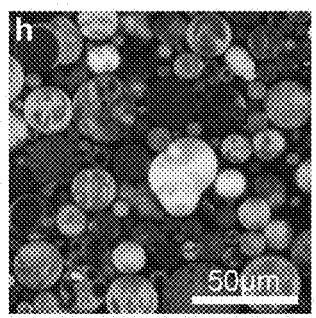
Figure 19I:
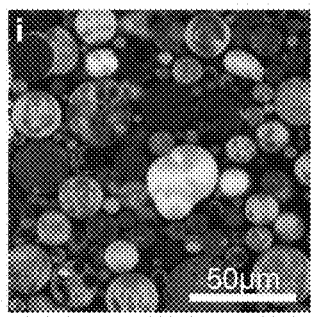
Figure 19J:
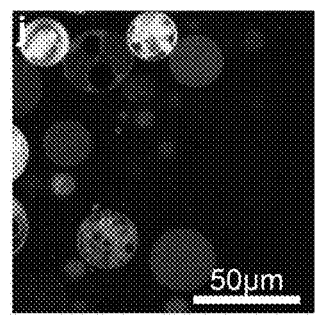
Figure 19K:
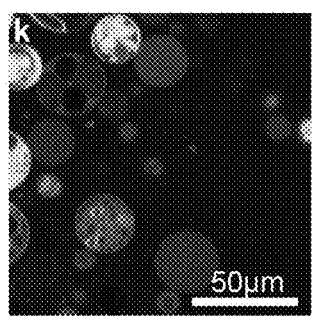
Figure 19L:
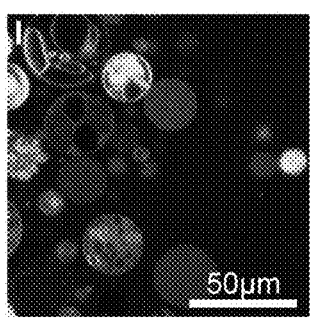
Figure 20A:
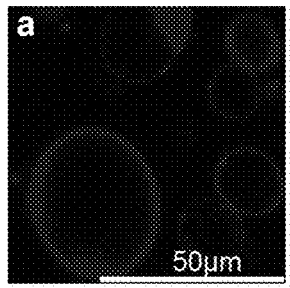
FIGS. 20A to 20L are confocal microscopy images that show selective dye leakage from *E. coli*-mimicking GUVs when interacting with nanostructured PMBs but not with the linear-chain P4MVP$_{28}$ (scale bar: 50 μm).
Figure 20B:
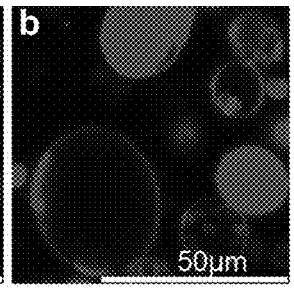
Figure 20C:
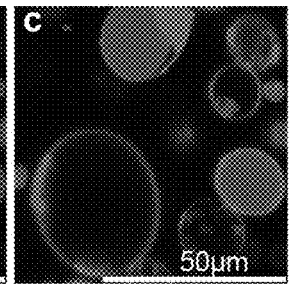
Figure 20D:
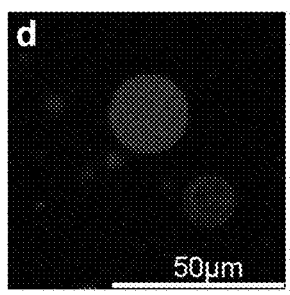
Figure 20E:
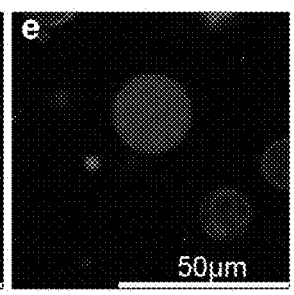
Figure 20F:
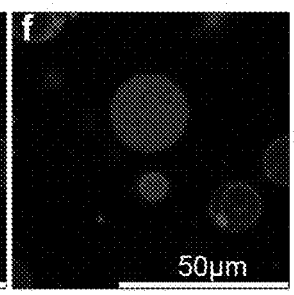
Figure 20G:
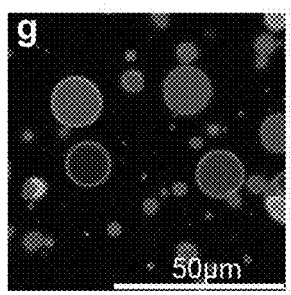
Figure 20H:
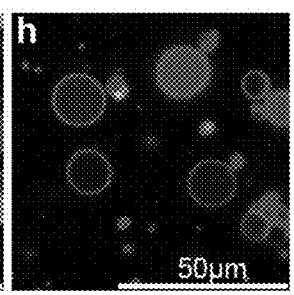
Figure 20I:
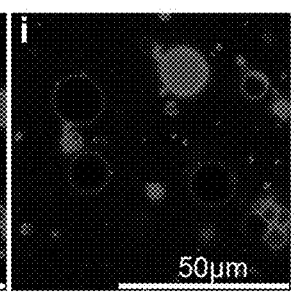
Figure 20J:
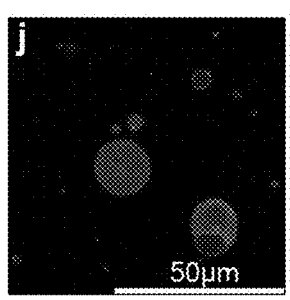
Figure 20K:
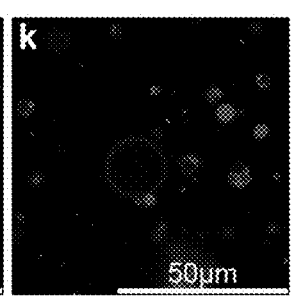
Figure 20L:
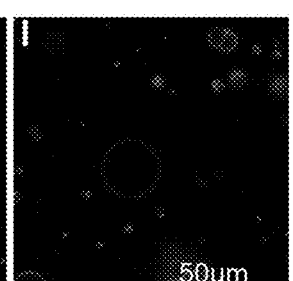

These hydrophilic phage-mimicking PMBs become potent antimicrobials against both Gram– and Gram+ bacteria including the clinical multidrug resistant bacterial strains without compromising their hemocompatibility by carrying hydrophobic moieties. Just like P4MVP$_{28}$, all PMBs show negligible hemolytic activity up to 512 µg/ml that we tested (FIG. 3D), hence a selectivity against bacteria over HRBCs as well. The hydrophilic P4MVP$_{28}$ and PMBs do differ greatly on hemagglutination: while the linear-chain P4MVP$_{28}$ causes severe coagulation of RBCs, nanostructured PMBs show little sign of hemagglutination (FIG. 18).

Selective Membrane Disruption Depends on Both Lipid Composition and the Polymer Nanostructure. The different action of P4MVP$_{28}$ and PMBs on bacteria and HRBCs underscores their distinctive multivalent interactions with host membranes. Mammalian and microbial membranes differ fundamentally in structure and lipid composition. To examine the effect of lipid composition, the inventors performed dye leakage experiments (FIG. 4A, FIG. 4B) using model giant unilamellar vesicles (GUVs) comprised of anionic lipid 1,2-dioleoyl-sn-glycero-3-phospho-(1'-rac-glycerol) (DOPG), and zwitterionic lipids 1,2-dioleoyl-sn-glycero-3-phosphocholine (DOPC) and 1,2-dioleoyl-sn-glycero-3-phosphoethanolamine (DOPE). Both DOPG and DOPC have zero intrinsic curvature, while DOPE has negative intrinsic curvature. As a simple but insightful model,[19] the inventors used 20/80 (molar ratio) DOPG/DOPE and DOPG/DOPC, respectively, to mimic the PE-rich E. coli and PC-rich mammalian membranes. Although the exact lipid compositions vary among different bacterial strains, they share the similarity of having a significantly higher population of lipids with negative intrinsic curvature (e.g., PE-lipid) than mammalian membranes.[64] PMBs and P4MVP$_{28}$ adhere onto both oppositely charged GUVs (FIGS. 19A-L, FIGS. 20A-L). They do not disrupt the mammalian-mimicking GUVs, as negligible dye leakage from these GUVs loaded with fluorescein is observed in the time frame (i.e. ~500s) that we tested (FIG. 4B, FIGS. 19A-L). The same is true for the P4MVP$_{28}$ when adhered to the E. coli-mimicking GUVs (FIG. 4A). In sharp contrast, all PMBs cause complete dye leakage to the E. coli-mimicking GUVs (FIG. 4A, FIGS. 20A-L). This result shows that selective membrane disruption occurs depending on both the lipid composition and polymer nanostructures. The mammalian-mimicking membranes maintain integrity after interacting with all polymers, while the E. coli-mimicking membranes are ruptured only by the nanostructured PMBs but not linear-chain P4MVP$_{28}$. Despite the limitation of dye leakage experiments,[19] this result agrees very well with the observed hemolytic and antimicrobial activity, and corroborates scanning electron microscopy (SEM) studies: the nascent morphology of E. coli (FIG. 4C) remains unchanged after incubated with the linear-chain P4MVP$_{28}$ (FIG. 4D), but bursts into pieces when incubated with the nanostructured L-rPMB (FIG. 4E) and sPMB (FIG. 4F) that are antimicrobial active to E. coli.

Figure 5D:
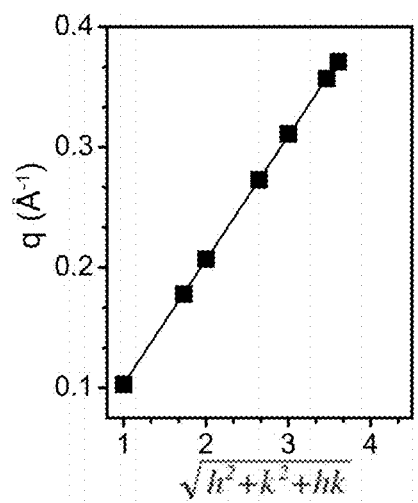

Nanostructure Helps Define the Antimicrobial Activity and Selectivity of Hydrophilic PMBs. To illuminate the mechanism of this nanostructure-dependent membrane remodeling, the inventors used synchrotron small angle x-ray scattering (SAXS) to track the structural evolution of both mammalian cell- and E. coli-mimicking liposomes incubated with PMBs and P4MVP$_{28}$. The unilamellar liposomes show a weak and broad SAXS peak characteristic of the liposome form factor.[19, 65] After interacting with the polymers, three diffusive SAXS harmonics (marked by ●) appear for the mammalian cell-mimicking liposomes at an increasing periodicity ranging from 56 Å ($q_{001}$=0.112 Å$^{-1}$) for P4MVP$_{28}$ to 59 Å ($q_{001}$=0.107 Å$^{-1}$) for L-rPMB, suggesting the formation of loosely stacked membranes tethered by the oppositely charged polymers (FIG. 5A). In reality though, mammalian cell membranes are asymmetric with an anionic inner leaflet but an zwitterionic outer one, hence unlikely attached to the polymers electrostatically. Nevertheless, when membrane charge density is kept the same (i.e. 20% anionic DOPG) but the zwitterionic DOPC is replaced with DOPE to mimic the E. coli membrane, completely different remodeling behavior is observed (FIG. 5B). For P4MVP$_{28}$, a series of sharp scatterings (marked by ○) at 0.102, 0.176, 0.204, 0.225, 0.270, 0.306, 0.336, 0.354, and 0.368 Å$^{-1}$ show up with a relationship of $\sqrt{2}$: $\sqrt{6}$: $\sqrt{8}$: $\sqrt{10}$: $\sqrt{14}$: $\sqrt{18}$: $\sqrt{22}$: $\sqrt{24}$: $\sqrt{26}$, which fit nicely the scatterings from a bicontinuous cubic phase (Im3m) also known as the "plumber's nightmare" (FIG. 5C). The only unaccounted peak is at 0.112 Å$^{-1}$ (marked by ●), which together with its two higher overtones at 0.225 and 0.336 Å$^{-1}$ (marked by ●)

coincident with the cubic scatterings suggests the co-existence of membrane stacks tethered by the oppositely charged $P4MVP_{28}$, possibly due to membrane de-phasing upon interacting with $P4MVP_{28}$. For the nanostructured PMBs, a completely new set of scatterings is observed. For L-rPMB, the peaks at 0.103, 0.178, 0.207, 0.273, 0.311, 0.357, and 0.371 Å$^{-1}$ (marked by ↓) fit nicely as the $q_{10}$, $q_{11}$, $q_{20}$, $q_{12}$, $q_{30}$, $q_{22}$, and $q_{31}$ scatterings, respectively, of a 2D hexagonal lattice with a unit cell of 70 Å (FIG. 5D). For sPMB, the same set of hexagonal peaks is observed but slightly red-shifted in q space, indicating a reduced lattice parameter (a=66 Å, $q_{10}$=0.110 Å$^{-1}$) likely due to a bit more brush compression when interacting with the membrane.

Figure 6A:
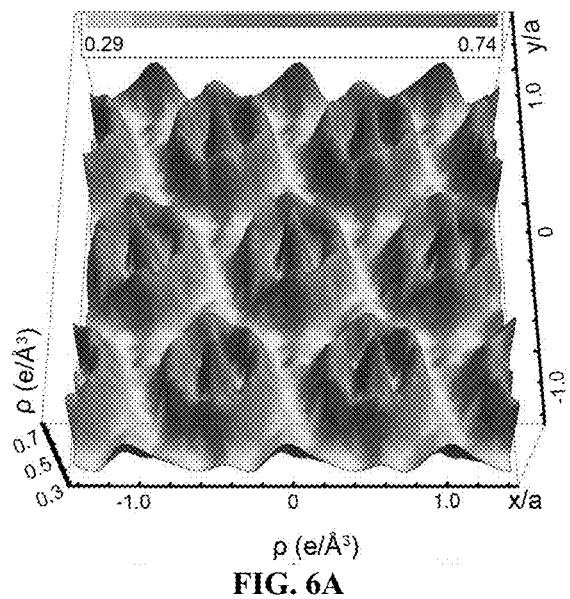
FIGS. 6A to 6C show that hydrophilic and nanostructured PMBs remodel bacterial membranes by inducing a topological transition to form membrane pores.
Figure 6B:
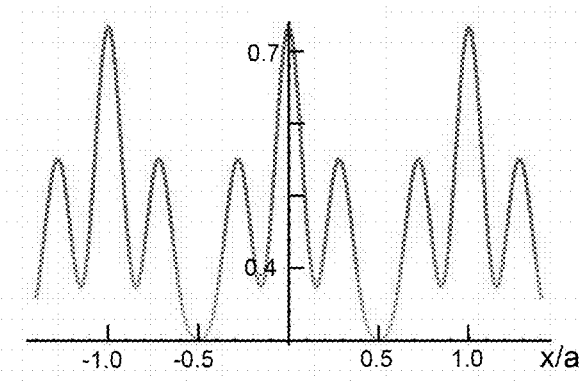

To determine how the nanostructured PMBs remodel bacterial membranes, the inventors performed Fourier reconstruction[66-68] to reveal the electron density maps in real space. Based on the phase criteria developed by Turner and Gruner,[67] our phase choices are (+−−++++). The electron density maps of the *E. coli*-mimicking membrane remodeled by L-rPMB at 3D (FIG. 6A) and 1D (FIG. 6B) revealed hexagonally patterned membrane pores ($H_{II}$): the region between the crater-like features has the lowest electron density (0.29 e/Å$^3$, shown in yellow) characteristic of the hydrophobic tails of lipids. At the center of each "crater" is a rod-like feature with the highest electron density (0.74 e/Å$^3$, shown in magenta), which can be only assigned to PMB because only the PMB has heavy iodides associated with its P4MVP branches. Encircling each PMB is a rim (d~42 Å) of an intermediate electron density (0.55 e/Å$^3$, shown in dark red) higher than that of a typical phospholipid headgroup (0.41 e/Å$^3$), suggesting the presence of residue iodides from the PMB. This close PMB-membrane interaction and the resultant deviation of its P4MVP branch conformation from an extended state to a compressed one is further confirmed by the diameter of the inverted membrane pores (i.e. 42 Å), which is smaller than the diameter of L-rPMB estimated based on the contour length of the $P4MVP_{29}$ branches (i.e. 70 Å). The Fourier reconstructed electron density maps of the *E. coli*-mimicking membrane remodeled by sPMB also revealed very similar membrane pore formation (FIGS. 21A-B), with a minor difference that the highest electron density corresponding to the position of sPMB at the center of each pore is lightly lower (0.71 e/Å$^3$).

Figure 6C:
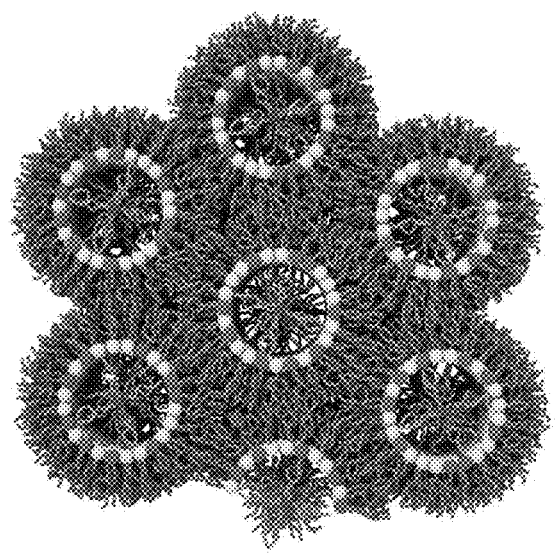

Small-angle X-ray scattering (SAXS) analysis clearly reveals how PMBs remodel bacterial membranes, as schematically illustrated in FIG. 6C. Both polymer nanostructure and lipid composition play important roles on selective membrane remodeling. Unlike mammalian cells, bacterial membranes are rich in lipids with negative intrinsic curvature (e.g., PE-lipid). As identified previously,[13, 30] the negative intrinsic curvature helps pore formation when bacteria interact with amphiphilic MAAs that breach the hydrophobic membrane interior. When bacteria interact with hydrophilic MAAs that stay on membrane surface, these data show that the negative-intrinsic-curvature lipids alone do not always favor the detrimental pore formation, as witnessed by the linear-chain $P4MVP_{28}$ that induces the formation of a membrane bicontinuous cubic phase and remains as a weak bactericide. Interestingly, the propensity for pore formation is greatly reinforced when nanostructured PMBs interact with the bacterial membranes. The inventors attribute this unusual reinforcement to the cooperative multivalent interactions that help bend bacterial membranes collectively around the nanostructures (FIG. 6C). This membrane topological transition is initiated by the attractive PMB-membrane electrostatic interactions but only proceeds with additional assistance from the negative-intrinsic-curvature lipids rich in bacterial membranes to offset the bending energy cost. It does not take place in mammalian membranes rich in zero-curvature lipids (FIG. 5A). By way of explanation, and in no way a limitation of the present invention, because of the hydrophilicity of PMBs, the inventors believe this mode of action does not breach the hydrophobic membrane interior, hence not fitting into any current model proposed for the actions of amphiphilic MAAs,[10-13] and shows that hydrophilic MAAs that selectively disrupt bacteria membranes but spare mammalian cells.

Bacterial Peptidoglycan Layer Is a Selective Filter for Nanostructured PMBs. Besides selectivity between bacterial and mammalian cells, PMBs also show selectivity between Gram+ and Gram− bacteria (FIGS. 3A to 3C, Table 1). The bacteria inhibitory activity of PMBs against all individual bacterial strains decreases from sPMB to S-rPMB and L-rPMB, likely due to the fact that they all adhere to the bacterial membranes and intervene in the bacteria homeostasis with a size- and shape-dependent efficiency. The bactericidal activity also decreases in a similar manner, showing a size- and shape-dependency on causing irreversible bacterial cell death. It is interesting to note that both forms of the antimicrobial activity decrease more rapidly against the Gram+ *S. aureus* and MU50 than the Gram− *E. coli* and PA14 when the overall size of PMBs gets bigger. This nanostructure-dependent antimicrobial selectivity of PMBs is further demonstrated by the bacteria live/dead assays (FIGS. 22A-C): while sPMB kills both Gram− *E. coli* and Gram+ *S. aureus* when the two bacteria coexist, L-rPMB selectively destroys the *E. coli* in the presence of *S. aureus*. The resultant double selectivity, i.e. selectivity between bacteria and mammalian cells as well as that between different families of bacteria, was reported before for certain amphiphilic SMAMPs, such as poly(norbornene),[24] and was attributed to their molecular weight difference: because *S. aureus* has a thick peptidoglycan layer outside its membrane, it was reasoned that only small molecular weight SMAMPs (e.g., <3 kD) can effectively penetrate this layer to disrupt *S. aureus* membrane. Other studies on amphiphilic polymeric SMAMPs and disinfectants didn't find any simple correlation between antimicrobial activity and molecular weight, except that high molecular weight polymers often exhibit increased hemolytic activity.[16-18] Given that the molecular weight of the model PMBs are orders of magnitude higher than most reported SMAMPs and polymer disinfectants, the observed double selectivity suggests that the size and shape of PMBs rather than their molecular weight per se help define their different activity against the two different families of bacteria. When the nanostructured PMBs interact with Gram− bacteria that have a thin peptidoglycan layer sandwiched between their outer and inner membranes, all model PMBs kill the bacteria by disrupting their membranes to form pores (FIG. 3A, 4E-4F, FIGS. 22A-C), and the thin peptidoglycan layer plays a limited role on restricting further penetration of PMBs to access the bacterial inner membrane; when PMBs interact with the Gram+ bacteria that have a thick peptidoglycan encapsulation, only the PMBs that can cross this selective filter gain access to the bacterial membrane and take actions (FIG. 3B, FIGS. 22A-C). The exact "mesh size" of the cross-linked peptidoglycan barrier of different bacteria was not known but estimated to range from 5-50 nm.[69-70] These results strongly support this finding, because the spherical sPMB (d~8.5 nm) can diffuse easily through this barrier to wreak havoc on all bacteria, while the rod-shaped rPMBs could get stuck on the cell wall surface and cause little bactericidal effect depending on their aspect ratios. For instance, the L-rPMB (1~70 nm; aspect ratio~10) shows moderate to high bactericidal activity against the Gram− *E. coli* and PA14, but zero bactericidal activity and a huge MBC (i.e. 512 µg/ml) against the Gram+ *S. aureus* and MU50, respectively; the S-rPMB (1~18 nm; aspect ratio~2.5) kills all bacteria with moderate to high activity; while the sPMB (d~8.5 nm; aspect ratio~1) shows extremely high activity against all bacterial strains.

Figures 7A, 7B, 7C, 7D:
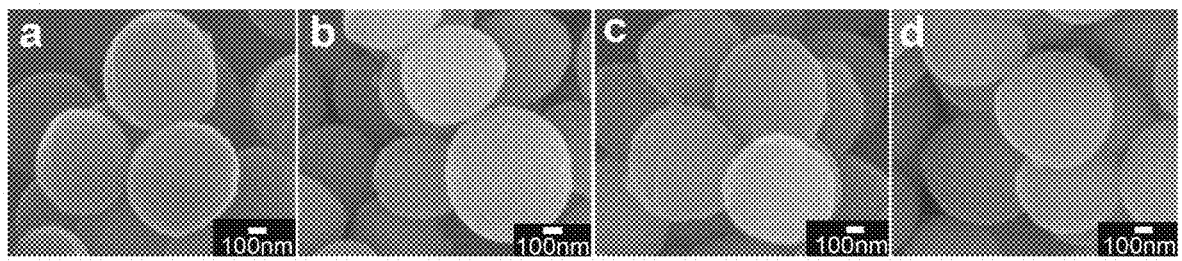
FIGS. 7A to 7H show peptidoglycan layer is a selective filter that helps define the different activity of nanostructured PMBs against different families of bacteria. Comparative SEM (FIGS. 7A to 7D) and cross-sectional TEM (FIGS. 7E to 7H) pictures of the Gram+ *S. aureus* control (FIG. 7A, FIG. 7E) and that incubated with P4MVP$_{28}$ (FIG. 7B, FIG. 7D), L-rPMB (FIG. 7C, FIG. 7G) and sPMBs (FIG. 7D, FIG. 7H), respectively, show that while no obvious morphology change (FIG. 7A-FIG. 7D) is observed when *S. aureus* interact with all polymers including the bactericidal sPMB, dramatic difference in plasma membrane disruption is revealed underneath the surface.
Figures 7E, 7F, 7G, 7H:
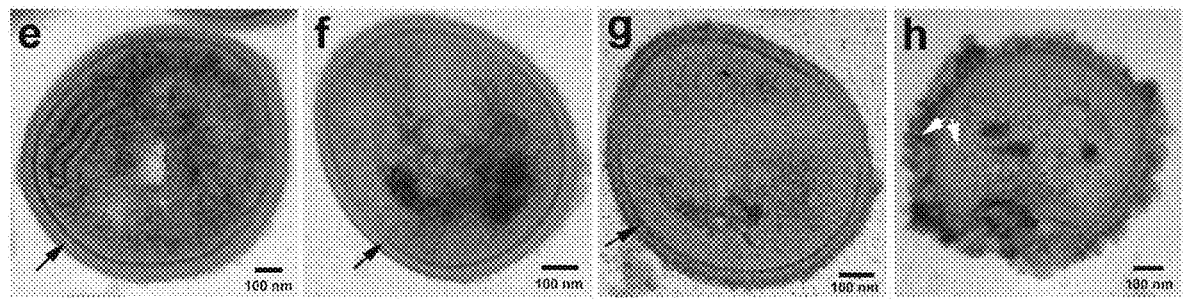

As further evidences to support this nanostructure-dependent antimicrobial selectivity as a result of the cell wall difference between Gram− and Gram+ bacteria, the inventors compared both SEM (FIGS. 7A to 7D) and cross-sectional transmission electron microscopy (TEM) images (FIGS. 7A to 7H) of the Gram+ *S. aureus* before and after incubated with P4MVP$_{28}$, L-rPMB, and sPMB, respectively. Unlike the Gram− *E. coli* (FIGS. 4C to 4F), no discernible morphology change of the *S. aureus* is observed even when incubated with the bactericidal sPMB (FIGS. 7A to 7D), indicating the robustness of its peptidoglycan encapsulation. Nevertheless, underneath the seemingly tranquil surface dramatic difference is revealed under cross-sectional TEM. For *S. aureus* control (FIG. 7E) and that incubated with non-bactericidal P4MVP$_{28}$ (FIG. 7F) and L-rPMB (FIG. 7G), the integrity of bacterial plasma membrane beneath the peptidoglycan layer (fixed by OsO$_4$ and marked by black arrows) persists; this is in sharp contrast to *S. aureus* incubated with the bactericidal sPMB (FIG. 7H), in which the plasma membrane is completely ruptured, and sPMBs that cross the peptidoglycan layer and reach the bacterial cytoplasm are seen (examples marked by white arrows). This result is consistent with our MBC and bacterial live/dead assays as well as SAXS analysis. Although all hydrophilic nanostructured PMBs can induce a topological transition of microbial membranes and cause membrane disruption, the L-rPMB, due to its large length and aspect ratio, is too big to cross the peptidoglycan encapsulation of Gram+ *S. aureus* to take actions (FIG. 7G). The linear-chain P4MVP$_{28}$ can cross the peptidoglycan layer but can't rupture the bacterial membrane due to the lack of nanostructure-associated multivalent interactions that help bend the membrane collectively around itself (FIG. 7F). This nanostructure-dependent double selectivity has not been identified before but holds promise to the development of nanostructured MAAs that kill target pathogen species without damaging other species of normal microbial flora.

In summary, the inventors used a biomimetic approach to determine the role of nanostructures on defining the activity and selectivity of MAAs. Compared to previous studies on various antibiotic nanostructures, the composition and methods taught herein differ in that well-defined hydrophilic nanostructures were synthetically manufactured via controlled/"living" polymerization, eliminating other contributions to the antimicrobial activity from amphiphilicity,[28-33, 42-51] the self-assembly and disassembly equilibrium between amphiphilic unimers and their nanostructures,[42-45] and nanoparticle reactivity.[52] It is further demonstrated herein that nanostructure is another important aspect in rendering MAAs with high activity, low toxicity, and target specificity because it recognizes both the membrane structure and lipid composition difference in mammalian and bacterial cells. On one hand, it gives rise to multivalent interactions that induce pore formation exclusively on microbial membranes, because only the charged microbial membranes laden with negative-intrinsic-curvature lipids are able to undergo a topological transition to bend themselves collectively around the nanostructures. Although this mode of damage may also contribute to the antimicrobial activity of various amphiphilic nanostructures[28-33, 42-51] including amphiphilic AMPs with well-defined secondary structures,[71-72] it does not need hydrophobic interactions as that exist in the amphiphilic nanostructures to breach the membrane interior, hence opening a door to transform diverse hydrophilic polymers that have excellent biocompatibility and low toxicity but weak antibiotic activity into potent nanostructured antimicrobials. On the other hand, the nanostructures respond to the cell wall difference of different families of bacteria. By controlling the size and shape of the nanostructures the inventors were able to control their selective access to Gram+, Gram−, or both bacterial membranes to take actions. These findings help resolve the long-standing dilemma that walks a fine line between the cationic-hydrophobic boundary in the hope of trading toxicity with antimicrobial activity, and point toward a potential paradigm shift to develop a new family of antibiotics, the nanoantibiotics, to fight tough pathogenic infections and thwart bacterial resistance. This rational design of nanoantibiotics with optimal activity, selectivity, biocompatibility, and biodistribution are possible from the nanoengineering and the use of bioorthogonal chemistry disclosed herein.

Materials. 2-Hydroxyethyl methacrylate (HEMA, 97%, inhibited with <250 ppm of monomethyl ether hydroquinone), 4-vinylpyridine (4VP, 95%, inhibited with 100 ppm of hydroquinone), iodomethane, ethyl iodide, butyl iodide, hexyl iodide, octyl iodide, and dodecyl iodide (98-99%, stabilized with copper), 1,1'-Azobis(cyclohexanecarbonitrile) (ACHN), 2,2'-Azobis(2-methylpropionitrile) (AIBN), copper(I) chloride (99%), copper(II) chloride (99.999%, trace metals basis), β-CD (≥97%), α-bromoisobutyryl bromide (BIBB, 98%), trimethylamine (TEA, ≥99%), 1-ethylpiperidine hypophosphite (EPHP, 95%), anhydrous N,N-dimethylacetamide, Dimethyl sulfoxide (DMSO, ≥99.5%), potassium phosphate monobasic (KH$_2$PO$_4$, ≥99%), agar, Triton X-100, fluorescein, and glutaraldehyde solution (50%) were purchased from Sigma-Aldrich (St. Louis, Mo.). Tris[2-(dimethyl amino) ethyl]amine (Me$_6$TREN, 99+%) was purchased from Alfa Aesar (Ward Hill, Mass.). Alexa Fluor® 647 C2 maleimide was purchased from Life Technologies (Grand Island, N.Y.). All other chemicals, unless otherwise discussed, were reagent grade and used as received from Sigma-Aldrich.

DOPG, DOPE, DOPC and 1,2-dioleoyl-sn-glycero-3-phosphoethanolamine-N-(lissamine rhodamine B sulfonyl) (ammonium salt) (18:1 Liss Rhod PE) were purchased from Avanti Lipid (Alabaster, Ala.) and used as received. The prototypical Gram− and Gram+ bacteria strains *E. coli* (ATCC 25922) and *S. aureus* (ATCC 25923) were purchased from American Type Culture Collection (ATCC) (Manassas, Va.), and reactivated according to the instructions from ATCC. The clinical multidrug resistant bacteria strains, i.e. the Gram− *Pseudomonas aeruginosa* (PA14, resistant to Tobramycin and Gentamycin) and Gram+ *S. aureus* (MU50, resistant to Methicillin, Oxacillin, and Vancomycin) were provided by Prof. Kendra Rumbaugh. Fresh human red blood cells (HRBCs) were purchased from Innovative Research Inc. (Novi, Mich.), stored at 4° C. and used within 2 weeks. Tryptic soy broth (TSB) and Mueller Hinton (MH) broth were both purchased from Becton, Dickinson and Company (BD) (Franklin Lakes, N.J.) and used as received.

HEMA and 4VP were purified by passing through a column packed with base aluminum oxide. ACHN and AIBN were purified by recrystallization in ethanol twice and dried in a vacuum oven at room temperature. Copper(I) chloride (CuCl) was purified by stirring in acetic acid at room temperature overnight. The RAFT polymerization chain transfer agent 4-Cyano-4-(dodecylsulfanylthiocarbonyl) sulfanyl pentanoic acid (CDTSPA) was synthesized as reported.[73]

Bacterial Killing Assay. The minimum bactericidal concentration (MBC) was determined following the method suggested by Clinical and Laboratory Standards Institute (CLSI) and literatures.[59-60] Bacteria were grown in MH broth at 37° C. for 18 h, and then diluted into fresh MH broth (100×) for re-growth. Bacterial growth was monitored by optical density at λ=600 nm ($OD_{600}$) using a UV-Vis spectrometer (Hewlett Packard 8435) (Palo Alto, Calif.). After the mid-log phase ($OD_{600}$=0.5-0.6) was reached, the bacteria were washed twice with sterile PBS buffer (10 mM $KH_2PO_4$, 150 mM NaCl, pH 7.0) and harvested by centrifugation at 10,000 rpm for 5 min. The harvested bacteria were re-suspended and diluted by PBS buffer to $1.5 \times 10^6$ CFU/mL within 15 minutes. This CFU size was determined by spreading serial diluted bacterial suspensions on agar plates.

To determine the MBCs, the PMBs and $P4MVP_{28}$ were first dissolved in DMSO and then dialyzed in sterile Millipore water for 2 days to give their stock solutions. Additional series of 2-fold dilution of the stock solutions by PBS buffer in microcentrifuge tubes gave a range of concentrations to be tested. To each well in a preset 96-well microplate, 100 μL of the diluted PMBs or $P4MVP_{28}$ solution at certain concentration and 50 μL of the diluted bacterial suspension were added, so that the final bacterial concentration is $\sim 5 \times 10^5$ CFU/mL. The positive control is 50 μL diluted bacterial suspension mixed with 100 μL buffer, and the negative control is 150 μL buffer by itself. The plates were incubated at 37° C. for 3 h. Serial 10-fold dilution was subsequently made with PBS buffer. For each dilution, 20 μL of the solution was taken and plated onto MH agar plates, which were then incubated at 37° C. overnight to yield visible colonies. The bacterial survival rate was calculated by dividing the number of colonies yielded from each bacterial grow solution at each PMB or $P4MVP_{28}$ concentration by that from the positive control. The negative control was used to eliminate the possibility that the PBS buffer was contaminated with the bacteria. The MBC was defined as the concentration of PMBs or $P4MVP_{28}$ at which at least 99.9% of bacteria are killed. All experiments were performed two times, each in triplicates, on different days, and the standard deviation (SD) to the averaged data at each polymer concentration was calculated.

Bacterial Inhibitory Assay. The minimum bacterial inhibitory concentration (MIC) was also determined following the method suggested by CLSI and literatures.[59-60] Bacteria were inoculated in MH broth and cultivated for 18 h at 37° C., and then diluted into fresh MH broth (100×) for re-growth. When $OD_{600}$=0.5-0.6 was reached, bacterial growth cultures were diluted by fresh MH broth to $5 \times 10^5$ CFU/mL. To determine the MICs, 10 μL diluted PMB or $P4MVP_{28}$ solution at different concentrations and 90 μL diluted bacterial suspension were added into each well in a preset 96-well microplate. For the positive control, 90 μL diluted bacterial suspension was mixed with 10 μL sterile water. For the negative control, 90 μL fresh MH broth was mixed with 10 μL sterile water. The 96-well microplates were then incubated at 37° C. for 18 h. After that the $OD_{560}$ was measured with a microplate reader (PerkinElmer Victor X5; Waltham, Mass.). The uninhibited growth rate ω was calculated by:

$$\omega = \frac{OD_{560,sample} - OD_{560,NC}}{OD_{560,PC} - OD_{560,NC}} \times 100\%,$$

where $OD_{560, sample}$ is the optical density of each bacterial growth culture at the presence of a defined PMB or $P4MVP_{28}$ concentration, $OD_{560, PC}$ is the optical density of the positive control and $OD_{560, NC}$ is the optical density of the negative control. The MIC is defined as the concentration of PMBs or $P4MVP_{28}$ that completely inhibited bacterial growth, i.e., no optical density difference was observed within experimental error when compared to the negative control.

Bacteria Live/Dead Assay. Besides using the MBC and MIC assays, we also used the bacteria live/dead staining kit (PromoCell GmbH, Germany) to visualize the antimicrobial selectivity of PMBs against a mixture of different families of bacteria. The staining kit contains fluorescent dyes DMAO (ex/em ~490/520 nm) and EthD-III (ex/em ~530/~635 nm) in DMSO. With an appropriate mixture of DMAO and EthD-III, bacteria with intact cell membranes (i.e. live) stain fluorescent green, whereas bacteria with damaged cell membranes (i.e. dead) stain fluorescent red. In a typical test, bacteria were first grown to mid-log phase ($OD_{600}$=0.5-0.7), harvested by centrifugation at 6000 rcf for 5 minutes, and washed with sterile PBS buffer (pH=7.4, 150 mM NaCl, 10 mM $NaH_2PO_4$) twice. The bacterial cells were then re-suspended in PBS buffer. A mixed suspension of *E. coli* and *S. aureus* was prepared by mixing both bacteria at an $OD_{600}$ ratio of 1/1. The bacteria mixture was diluted to OD=0.2 and incubated with sPMB or L-rPMB solutions for 3 h. The ratio of the amount of polymer versus the amount of bacteria was adjusted to be roughly the $MBC_{E. coli}/(5 \times 10^5$ CFU/mL). The mixed bacteria incubated with PBS buffer without PMBs were used as controls. After the incubation, the mixed bacteria were washed and suspended by Tris buffer (pH=7.4, 150 mM NaCl, 10 mM Tris). The staining kit was applied to the suspension and incubated for 15 min following the instruction provided by the manufacture. The final dye concentration in suspension was 5 μM DMAO and 4 μM EthD-III. The bacteria were washed and re-suspended with Tris buffer. 10 μL of suspension was imaged under a Nikon laser scanning confocal microscope (Nikon T1-E microscope with A1 confocal and STORM super-resolution modules) using a 100× oil-immersion objective lens.

Hemolysis and Hemagglutination Assays. The toxicity of PMBs and $P4MVP_{28}$ was assessed by their hemolytic and hemagglutination activities against HRBCs following the established protocols.[24, 27] For the hemolysis assay, the inventors first conducted a series of 2-fold dilution of the PMBs or $P4MVP_{28}$ stock solutions with PBS buffer to give a range of concentrations to be tested. Fresh HRBC suspension (300 μL) was washed twice with PBS buffer (12 mL) and harvested by centrifugation at 3,000 rpm (~1000 rcf), then re-dispersed in PBS buffer (15 mL) to reach a HRBC concentration of ~0.5%. Aliquots of this HRBC suspension (160 µL) were then mixed with PMBs and P4MVP$_{28}$ solutions (40 µL) in 1.5 ml micro-centrifugation tubes. The tubes were secured in an orbital shaker, and incubated at 37° C. at 250 rpm for 60 min. The inventors used PBS buffer (40 µL) and Triton X-100 (40 µL, 1% v/v) mixed with HRBC suspension (160 µL) as negative and positive controls, respectively. The tubes were subsequently centrifuged at 3000 rpm (~1000 rcf) for 5 minutes. Supernatant (30 µL) of each test sample was diluted with PBS buffer (100 µL) and put in individual wells of a 96-well microplate. The absorbance at 405 nm was measured with a microplate reader. The percentage of hemolysis ($\Psi$) was calculated by:

$$\psi = \frac{OD_{405,sample} - OD_{405,NC}}{OD_{405,PC} - OD_{405,NC}} \times 100\%,$$

where $OD_{405, sample}$ is the absorbance of HRBC suspension at the presence of a defined PMB or P4MVP$_{28}$ concentration, $OD_{405,PC}$ is the absorbance of the positive control and $OD_{405,NC}$ is the absorbance of the negative control. HC$_{50}$ is defined as the PMB and P4MVP$_{28}$ concentration that causes 50% hemolysis. This is commonly regarded as the index of toxicity, and the selectivity of antimicrobial agents against bacteria over mammalian cells is defined as HC$_{50}$/MIC.[20-26]

For the hemagglutination assay, fresh HRBC suspension (600 µL) was washed twice with PBS buffer (12 mL) and harvested by centrifugation at 3,000 rpm (~1000 rcf), then redispersed in PBS buffer (15 mL) to reach a HRBC concentration of ~1.0%. Aliquots of this HRBC suspension (800 µL) were then mixed with 512 µg/mL PMBs or P4MVP$_{28}$ solutions (200 µL) in a 24 well microplate. PBS buffer (200 µL) mixed with HRBC suspension (800 µL) was used as negative controls. The microplate was secured in an orbital shaker, and incubated at 37° C. and 250 rpm for 60 min, and settled for another 60 min before photo recording to visually inspect the aggregation of HRBCs (FIG. 18).

Confocal Microscopy. The inventors prepared GUVs following a previous report.[19] To prepare Rhodamine-labeled GUVs, a mixture of lipids solution (DOPG/DOPE=20/80 or DOPG/DOPC=20/80 molar ratio, in chloroform at 20 mg/mL) that contains 0.25 mol % 18:1 Liss Rhod PE was first prepared. 20 µL of this mixture was spread on to a roughened and cleaned Teflon slice and dried in vacuum. After pre-hydrated under a N$_2$ flow saturated with 50° C. water vapor for 15 min, 5 mL of 100 mM sucrose was added as the swelling solution and incubated for 2-3 days. The inventors used a similar procedure to prepare Fluorescein-incorporated and Rhodamine-labeled GUVs for the dye leakage experiments except that in the last step, 5 mL of 100 mM sucrose that contains 40 µM Fluorescein was added as the swelling solution.

The PMBs and P4MVP$_{28}$ labeled by Alexa 647 were prepared by a "click" reaction between maleimide-functionalized Alexa Fluor® 647 dye (1.4 nmol) and SH-terminated PMBs and P4MVP (10 mg, 0.14 µmol), which were obtained by reducing the trithiocarbonate end of either PMB or P4MVP$_{28}$ prepared by the RAFT polymerization method with hexylamine in DMSO. To characterize the localization of PMBs or P4MVP$_{28}$ on GUVs, 20 µL GUV suspensions in 100 mM sucrose was diluted into 80 µL 120 mM glucose. After the GUVs were settled, 10 µL 1 mg/mL Alexa 647 labeled PMBs or P4MVP$_{28}$ solution was added. We used either a laser scanning confocal microscopy (Olympus Fluoview FV10i; Waltham, Mass.) or a Nikon T1-E microscope with A1 confocal and STORM super-resolution modules (Nikon Inc., Melville, N.Y.) to locate the fluorescently labeled PMBs, P4MVP$_{28}$ and GUVs, respectively. The 653 nm and 558 nm lasers were used to excite Alexa 647 and Rhodamine, respectively, at a low intensity to avoid bleach of the dyes. Images were recorded as 1024×1024 pixel using a 60× objective lens and a CCD camera.

For dye leakage characterization, 20 µL of GUVs suspension in 100 mM sucrose was diluted into 80 µL 120 mM glucose. After the GUVs were settled on a glass slide, 10 µL 1 mg/mL PMB or P4MVP$_{28}$ sample solution was added at time zero. The fluorescence change of the GUVs over time was recorded at a time interval of 30 s. Lasers at 494 nm and 558 nm, respectively, were used to excite fluorescein and Rhodamine at low laser intensity. We used ImageJ to integrate the fluorescence intensity of individual GUVs in each frame recorded at different times. The background of each frame was also integrated and subtracted from fluorescence intensity of GUVs. The percentage of dye retention was calculated by taking the ratio of the background-subtracted fluorescence intensity at different times to that at time zero. Error bars (standard deviation; SD) were generated by analyzing the dye retention results from many GUVs in each determination.

SEM. The method for characterization of bacterial cells by SEM was modified from a previous report.[42] The bacterial suspension was first grown to mid-log phase (OD$_{600}$=0.5-0.6) and the cells were harvested by centrifugation at 5000 relative centrifugal force (rcf) for 10 minutes and washed with sterile PBS buffer twice. The bacterial cells were then re-suspended in PBS buffer and incubated with different polymer solutions (i.e., PMBs or P4MVP$_{28}$) for 3 h. For the bactericidal polymer, the ratio of the amount of polymer versus the amount of bacteria was adjusted to be roughly its MBC/(5×10$^5$ CFU/mL). For polymer that does not show MBC, its concentration was the same as the highest MBC of other bactericidal polymers in order to make the result comparable. Bacteria incubated with blank solutions that do not contain PMBs or P4MVP$_{28}$ were used as controls.

After the incubation, bacteria suspensions were washed by PBS buffer twice and then fixed by the PBS buffer containing 2.5% glutaraldehyde solution for 24 h. Finally, the fixed bacteria cells were further washed with sterile Millipore water for three times, followed by dehydration using a series of ethanol washes and dried in a lyophilizer. The fixed and dried bacterial cells were placed on a carbon tape, which was mounted onto an aluminum stud, and coated with a thin layer of gold prior to SEM analyses using a JEOL JSM7000F Field Emission SEM (Peabody, Mass.) with an accelerating voltage of 20 kV and a medium probe current.

TEM. The bacteria growth and incubation with different polymer samples or controls are as described above. After the incubation, bacteria suspensions were washed by PBS buffer twice and then fixed by 2.5% glutaraldehyde solution in PBS buffer for 24 h. After washing away excess glutaraldehyde by PBS buffer, the bacterial cells were further fixed with 1% osmium tetraoxide (OsO$_4$) in PBS buffer for 1 h, followed by 2 times wash with PBS buffer to remove excess OsO$_4$. After serial dehydration with 25%, 50%, 75%, 90%, 100% of ethanol, bacterial cells were then infiltrated with a solution of LX112 resin/acetone (weight ratio 1/2) for 2 h. The LX112 resin was composed of LX112, DDSA (dodecenyl succinic anhydride) and NMA (nadic methyl anhydride) at a mass ratio of 1.8/1/0.9. 0.14% (v/v); accelerator DMP-30 (2,4,6-tris(dimethylaminomethyl) phenol) was added to the resin mixture right before use. The bacterial cells were further infiltrated with solutions of LX112 resin/acetone=1/1, LX112 resin/acetone=2/1 and 100% LX112 resin for 2 h, respectively. Finally, bacterial cells were embedded in 100% LX112 resin and polymerized in 65° C. for 2 days. The solidified resin block was cut into pieces of ~80 nm thickness with ultramicrotome (Reichert-Jung Ultracut E) equipped with a diamond blade. The pieces containing the bacterial sections were stain by 4% uranyl acetate and Reynolds' lead citrate, and then placed on 200 mesh copper grids, followed by imaging with a Hitachi H-8100 TEM equipped with an AMT digital side mount camera.

Small-angle X-ray scattering (SAXS). Small unilamellar vesicles (SUVs) of liposomes with different lipid compositions mimicking bacterial or mammalian cell membranes were prepared as previously reported.[74-75] Briefly, different lipid mixtures were prepared by mixing lipid stock solutions prepared at defined concentrations in chloroform or chloroform/methanol solvent. The organic solvent was evaporated by a dry $N_2$ flow, and the resultant lipid films were further dried in a vacuum. Millipore water was then added to hydrate the lipid films and the final liposome concentrations were adjusted to be 20 mg/mL. After incubated in 37° C. overnight, the solutions were sonicated by a probe sonicator (Sonics Vibra Cell™; Newtown, Conn.) to clarity and extruded through an Avanti mini-extruder set equipped with a polycarbonate membrane (0.1 µm pore size) for 11 times to obtain uniformly-sized SUVs. All experiments were carried out at room temperature, which was much higher than the gel-liquid phase transition temperature for any of the individual lipids ($T_m$ (° C.): DOPG, -18; DOPE, -16; DOPC, -20), so there was no phase separation in the liposome membranes.[74]

The inventors prepared self-assembled complexes comprised of different liposomes and PMBs or P4MVP at stoichiometric ratios above, equal, and below their isoelectric point (i.e. +/−=5/1; 1/1; and 1/5). The complexes were subsequently transferred and sealed into quartz capillaries (diameter=1.5 mm; Hilgenberg GmbH, Germany), and measured at SSRL (Stanford Synchrotron Radiation Lightsource). Incident synchrotron x-rays from an eight-pole Wiggler was monochromatized ($\lambda$=1.37776 Å) and focused using a cylindrical mirror, and the scattered radiation was collected using a Rayonix MX225-HE detector (pixel size 73.2 µm, 3072 by 3072 array). A typical radiation time at SSRL is 5 s, and each sample was measured five times. No radiation damage was observed for all measurements, and we didn't observe structural variations of the same polymer-lipid complexes at different polymer-to-lipid stoichiometric ratios.

The 2-D SAXS powder patterns were integrated using FIT2D (www.esrf.eu/computing/scientific/FIT2D/), and the sample-to-detector distance was calibrated using silver behenate as a standard. The final SAXS data of individual samples were averaged over the five different measurements. For a subset of SAXS data revealing the 2D hexagonal pattern of remodeled membranes, we reconstructed the real-space electron density map following algorithms developed for the Fourier reconstruction as reported previously.[66-68]

Partition Coefficient. The inventors measured the octanol/water partition coefficient (P) of PMBs and P4VP$_{28}$ quaternized with alkyl iodides of different chain length to quantitatively characterize their hydrophilicity. To a 15 mL centrifuge tube, 2 mL octanol was added to 2 mL polymer solution (50 µg/mL). The mixture was gently mixed for 18 h and allowed to settle for another 18 h. For control, 2 mL octanol was mixed with 2 mL Millipore water. Since the pyridine moiety in all polymers has an absorption peak around 260 nm, the OD$_{260}$ of both the octanol layer and the water layer was measured. The partition coefficient was determined according to:

$$P = \left[ \frac{OD_{260, oil, sample} - OD_{260, oil, blank}}{OD_{260, water, sample} - OD_{260, water, blank}} \right]$$

where $OD_{260, oil, sample}$ was the absorbance of octanol layer of the tested sample, $OD_{260, oil, blank}$ was the absorbance of octanol layer of blank, $OD_{260, water, sample}$ was the absorbance of water layer of the tested sample, $OD_{260, water, blank}$ was the absorbance of water layer of blank. A negative log P indicates that the polymer sample is hydrophilic, while a positive log P indicates it is hydrophobic. As expected, all PMBs and P4VMP$_{28}$ are hydrophilic, and the nanostructured PMBs have even slightly more negative log P than the linear-chain P4VMP$_{28}$. Meanwhile, when the hydrophobic group in the alkyl iodides used to quaternize the linear-chain P4VP$_{28}$ increases from methyl to butyl, hexyl, and dodecyl, their log P values were continuously increased from negative to positive, indicating their increasing hydrophobicity.

Other Characterization Methods. The chemical structure of synthesized polymers was characterized by 1H and 13C NMR (400 M and 500 M JEOL NMR spectrometers) and FTIR spectroscopy (Thermo-Electron Nicolet 4700 spectrometer). The molecular weight and molecular weight distribution were measured by GPC either on a Viscotek GPCmax VE-2001 chromatograph equipped with Viscotek Model 270 Series differential viscometer/low angle laser light scattering detectors and a refractive index detector Model 3580, or an Agilent 1260 HPLC system equipped with a diode array UV detector, a Wyatt Optilab REX refractive index detector, and a Wyatt miniDAWN TREOS multi-angle light scattering detector.

Synthesis. Hydrophilic Phage-Mimicking Membrane Active Antimicrobials Reveal Nanostructure-Dependent Activity and Selectivity.

Synthesis of Well-Defined Spherical Polymer Molecular Brush β-CD-g-P4MVP28 (sPMB). The reaction scheme to prepare well-defined spherical PMB is shown in Scheme 1. Briefly, we prepared spherical PMB by converting the 21-OH β-cyclodextrin (β-CD) into a macro-initiator for atom transfer radical polymerization (ATRP)[1] of poly(4-vinylpyridine) (P4VP) branches, which were then converted to hydrophilic and cationic poly(4-vinyl-N-methylpyridine iodide) (P4MVP) via a quaternization reaction.[2] We used GPC, NMR, and FTIR spectroscopy together with brush cleavage experiments to determine the brush size, graft density, and the degree of quaternization.

Figure 8:
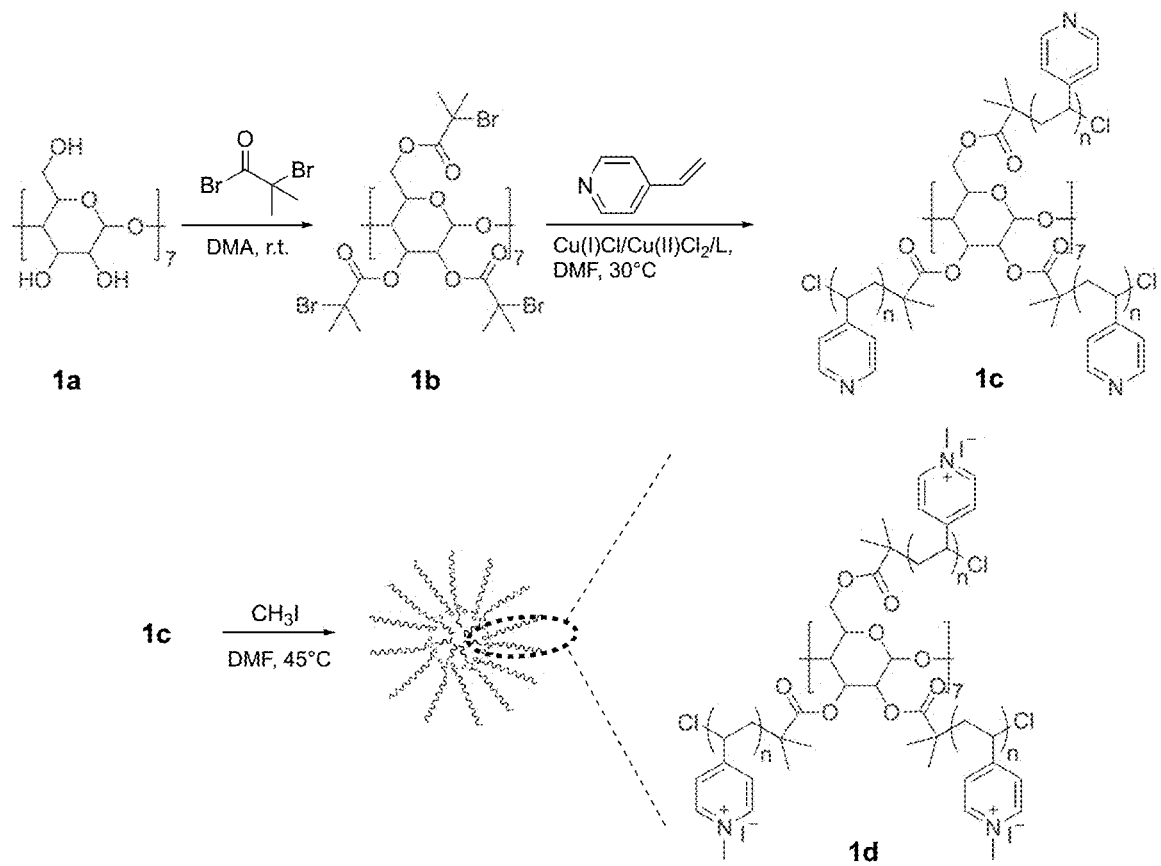
FIG. 8 shows chemical scheme S1. The reaction scheme to synthesize spherical PMB, β-CD-g-P4MVP.

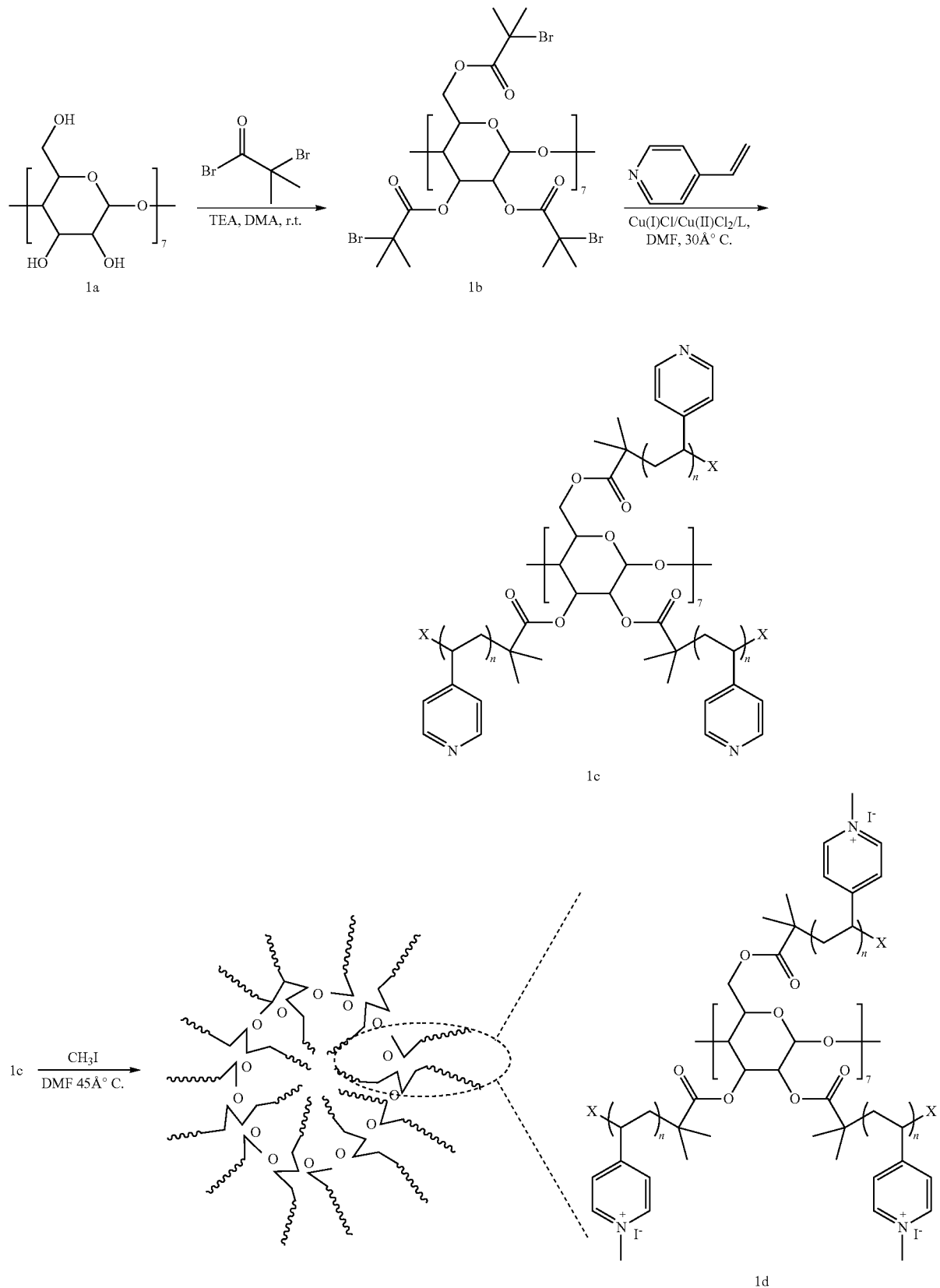
FIG. 8. Scheme S1. The reaction scheme to synthesize spherical PMB, β-CD-g-P4MVP.

The inventors introduced the ATRP initiation sites onto β-CD (1a) by dissolving β-CD (5.68 g, 5 mmol, vacuum-dried in a 100° C. oven in the presence of calcium oxide overnight prior to use) in 50 mL of anhydrous N, N-dimethylacetamide under nitrogen protection. The reaction mixture was stirred at 0° C. and α-bromoisobutyryl bromide (48.0 g, 210 mmol) was then added drop-wise to the β-CD solution over a period of 30 min. The reaction temperature was maintained at 0° C. for 2 h and then slowly increased to room temperature for 22 h. The brown reaction mixture was concentrated by blowing solvent away with air. The resultant crude product was diluted with 100 mL dichloromethane, and then washed sequentially with saturated NaHCO$_3$ aqueous solution (3×150 mL) and de-ionized water (3×150 mL). MgSO$_4$ was added to remove trace water and subsequently removed by filtration. The filtrate was collected and dried in a vacuum oven, and then crystallized in cold n-hexane to produce an orange product, heptakis[2,3,6-tri-O-(2-bromo-2-methylpropionyl]-β-cyclodextrin (Br-β-CD, 1b).

After the successful synthesis of Br-β-CD was confirmed by $^1$H NMR (FIG. 11A) and FTIR spectra (FIG. 11B), the Br-β-CD was used as a macroinitiator to synthesize the spherical PMB, β-CD-g-P4VP (1c), via ATRP. In a typical run, a mixture of Br-β-CD (42.6 mg, 0.21 mmol initiating sites), CuCl$_2$ (14.9 mg, 0.11 mmol), Me$_6$TREN (25.0 mg, 0.11 mmol), 4VP (4.41 g, 42 mmol), and DMF (6.0 g) was placed in a 25-mL Schlenk flask equipped with a magnetic stir bar. After degassed by three freeze-pump-thaw cycles, a mixture of CuCl (9.9 mg, 0.10 mmol), Me$_6$TREN (23.0 mg, 0.10 mmol) and DMF (2.8 g) was injected into the solution under a nitrogen flow. The flask was sealed after three more freeze-pump-thaw cycles and immersed in a constant temperature bath at 30° C. for 3 h. The polymer product, β-CD-g-P4VP (1c), was collected by precipitating in 10-fold acetone and dried in a vacuum oven overnight. The product was then reacted with excess iodomethane in DMF at 45° C. for 2 days to convert the P4VP branches into hydrophilic and cationic P4MVP. The reaction mixture was finally precipitated in 10-fold diethyl ether. The hydrophilic and cationic PMB product, β-CD-g-P4MVP (1d), was collected by centrifugation and dried in a vacuum oven overnight.

Besides characterizing the successful synthesis of products 1b through 1d using $^1$H NMR and FTIR spectra, we also characterized the size of individual P4VP branches by cleaving them from the β-CD core. In a typical cleavage experiment, 30 mg of spherical PMB, β-CD-g-P4VP, in 3 ml of DMF were mixed with 0.5 ml of 5 M KOH (in methanol) solution. The mixture was sealed and heated at 60° C. for 48 h. The resultant crude products were poured into 100 mL of dichloromethane and washed with saturated saline aqueous solution for 5 times. MgSO$_4$ was then added to remove trace water. After the MgSO$_4$ was filtered off, the filtrate was precipitated in diethyl ether for three times and dried in a vacuum oven.

Characterization Results. The β-CD-based ATRP macroinitiator was prepared by directly esterifying the 21 hydroxyl groups on β-CD (1a) with α-bromoisobutyryl bromide. The successful synthesis of Br-β-CD (1b) was confirmed by FTIR and $^1$H NMR (FIGS. 11A to 11E).

Figure 11A:
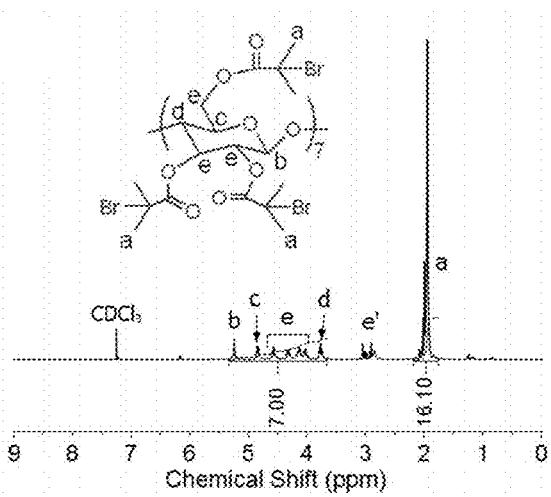
FIGS. 11A to 11E show the successful synthesis of the spherical sPMB, β-CD-g-P4MVP$_{28}$.
Figure 11B:
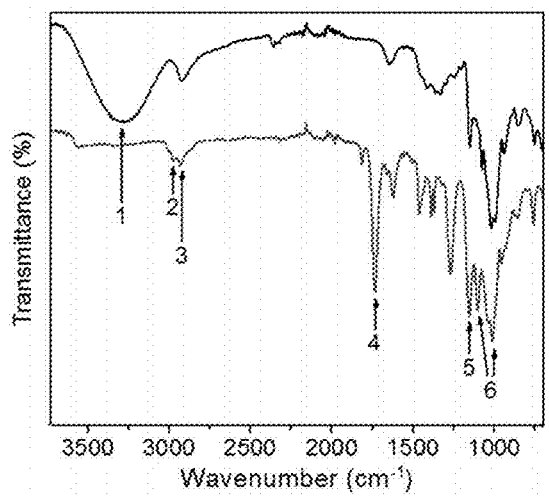
Figure 11C:
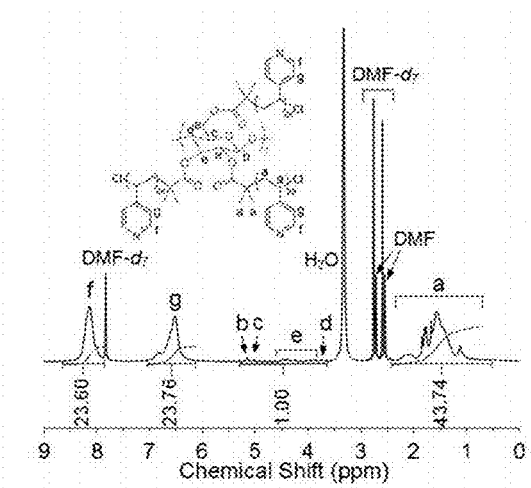

The extent of substitution of the 21-OH groups was determined by $^1$H NMR as shown in FIGS. 11A to 11E. The peak located at a chemical shift of δ=1.95 ppm is assigned to the methyl protons (FIG. 11A) of the α-bromoisobutyryl groups. The peaks within the range of chemical shifts of δ=3.6~4.7 ppm are attributed to methylidyne and methylene protons (FIG. 11C, FIG. 11D, FIG. 11E) between the oxygen and carbon moieties on the glucose units of β-CD. The peaks located at a chemical shift of δ=5.27 ppm are assigned to the methylidyne protons between the oxygen moieties (FIG. 11B). The peak in the region of chemical shifts δ=2.87~3.10 ppm is attributed to the methylidyne protons (e', CH—OH) adjacent to the unreacted hydroxyl protons on the glucose units of β-CD. The hydroxyl group conversion can be calculated from equation (1):

$$E_T = \frac{7A_a}{18(A_b + A_c + A_d + A_e)} \times 100\% \qquad (1)$$

where $E_T$ is the extent of substitution of the 21-OH groups on the glucose units of β-CD; $A_i$ is the integral area of peak i. Note that contribution from the integral area of peak e' is accounted for by that of the equal amount of unreacted hydroxyl protons under peak e in equation (1), hence is not included in the equation. Our analysis shows that 89.4% of the 21-OH groups on the β-CD core are substituted with α-bromoisobutyryl groups.

The successful synthesis of Br-β-CD was also confirmed by FTIR (FIG. 11B), in which a series of new characteristic peaks belonging to Br-β-CD appeared after the synthesis: 2974 cm$^{-1}$ (peak 2, $\nu_{CH3}$), 2927 cm$^{-1}$ (3, $\nu_{CH2}$), 1735 cm$^{-1}$ (4, $\nu_{C=O}$), 1155 cm$^{-1}$ (5, $\nu_{C—O—C}$), 1034 cm$^{-1}$ and 1105 cm$^{-1}$ (6, coupled $\nu_{C—C}$ and $\nu_{C—O}$). The disappearance of the stretching vibration of —OH groups on β-CD centered at 3290 cm$^{-1}$ (1) is also evident after the synthesis.

The spherical PMB β-CD-g-P4VP (1c) was prepared by ATRP of 4VP from Br-β-CD macroinitiators in DMF using Me$_6$TREN/CuCl/CuCl$_2$ as the catalyst complex. The inventors used a combination of characterization methods including $^1$H NMR, GPC and reaction conversion analysis to confirm the successful synthesis of β-CD-g-P4VP, and determined that the P4VP branches have a degree of polymerization (DP) of 28.

In $^1$H NMR spectrum (FIG. 11C), characteristic peaks for protons on pyridine rings of P4VP are shown as peak f and g. The average size of P4VP branches was determined by comparing the integral areas of peak f or g with all methylidyne and methylene protons on the glucose units of β-CD located within a chemical shift range of 3.6~5.3 ppm (peaks b, c, d, and e), assuming 100% grafting of P4VP branches on the 21-OH β-CD core. As shown in equation (2), n is the number of 4VP units on each P4VP branch and $A_i$ is the integral area of peak i:

$$n = \frac{7A_f}{2 \times 3(A_b + A_c + A_d + A_e)} \qquad (2)$$

The result indicated that each P4VP branch contains ~28 units. This analysis of reaction conversion also suggested a DP of 28. The DPs determined by $^1$H NMR analysis and reaction conversion agree with each other.

Figure 11D:
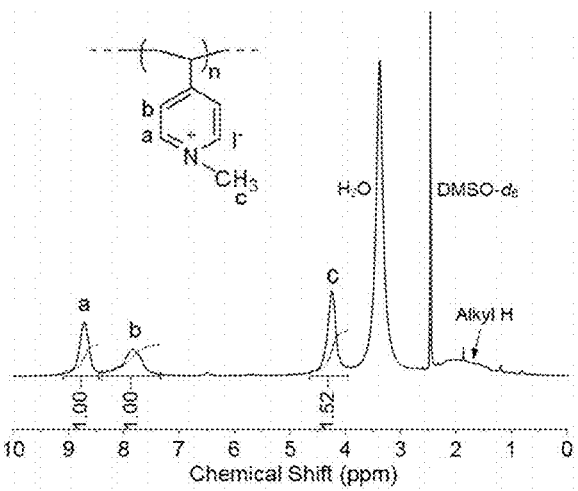

The successful synthesis of 100% quaternized spherical PMB, β-CD-g-P4MVP$_{28}$ (1d) was characterized by $^1$H NMR (FIG. 11D). After the β-CD-g-P4VP$_{28}$ was converted to its hydrophilic and cationic form by a quaternization reaction with CH$_3$I, the characteristic peaks of the protons on the pyridine moieties of 4VP units shift completely to 8.75 ppm and 7.92 ppm, respectively, from 8.33 ppm and 6.41 ppm (FIG. 11D).

Figure 11E:
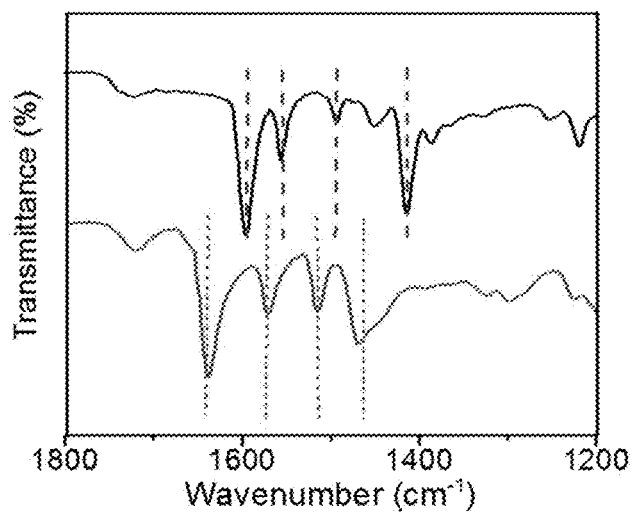

The inventors confirmed the 100% quaternization of CD-g-P4MVP$_{28}$ by FTIR (FIG. 11E). The main characteristic peaks of the pyridine moieties of 4-VP units (at 1595 cm$^{-1}$, 1554 cm$^{-1}$, 1494 cm$^{-1}$ and 1414 cm$^{-1}$, labeled with green dotted lines) shift completely to higher wavenumbers (at 1639 cm$^{-1}$, 1570 cm$^{-1}$, 1515 cm$^{-1}$, and 1468 cm$^{-1}$, respectively, labeled with pink dotted lines) after the quaternization.

Figure 12A:
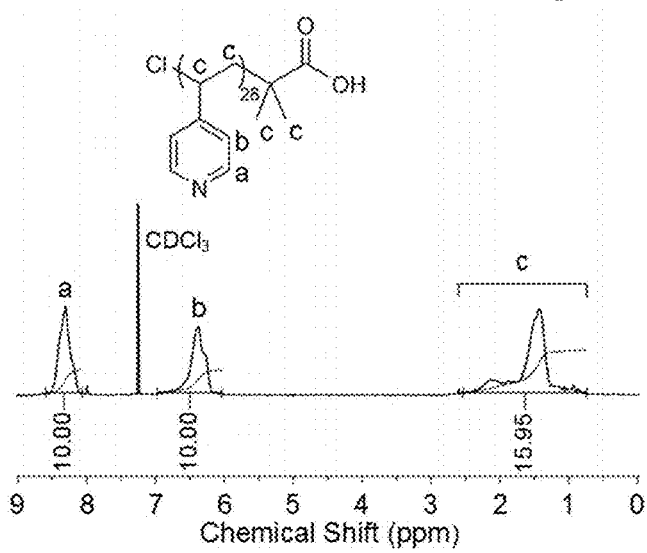
FIGS. 12A to 12B show brush cleavage experiment that reveals a P4VP graft density of 90% on the spherical sPMB.
Figure 12B:
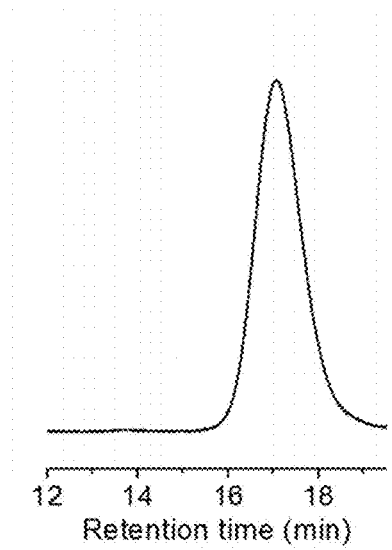

Finally, the inventors characterized individual P4VP branches by cleaving them from the β-CD core using a strong base. The structure and molecular weight of cleaved P4VP branches were confirmed by both $^1$H NMR and GPC studies (FIGS. 12A-12B). For $^1$H NMR analysis (FIG. 12A), the DP of cleaved P4VP branches was determined by comparing the integral areas of protons on pyridine rings of P4VP (peak a or b) with all alkyl protons (peak c). As shown in equation (3), n is the number of 4VP units on each P4VP branch and $A_i$, is the integral area of peaks i.

$$\frac{A_c}{A_a} = \frac{3n+6}{2n} \quad (3)$$

The inventors calculated the DP of cleaved P4VP branches to be ~31. This number is very close to the P4VP branch sizes obtained by 1H NMR analysis of β-CD-g-P4VP28 (FIG. 11C), as well as GPC measurement of the cleaved P4VP branches (FIG. 12B): GPC reports a molecular weight (Mn) of 3040 Da (i.e., DP=29) and a focused polydispersity index (PDI) of 1.19. Taken together, our characterization results confirmed the successful synthesis of well-defined spherical PMB, β-CD-g-P4MVP28.

The inventors further estimated the grafting density of P4VP branches on the PMB, which is defined as the percentage of the 21-arms on Br-β-CD core that successfully graft a P4VP chain. This estimation is based on the comparison of the P4VP molecular weight obtained by 1H NMR analysis of β-CD-g-P4VP28 and P4VP branches, respectively, indicated a graft density of ~90%. This number is close to ET (i.e. the extent of substitution) of ATRP initiator sites on the β-CD core, suggesting that each ATRP initiator site on the β-CD core successfully initiated the polymerization of a well-defined P4VP branch.

Synthesis of Well-Defined Long Rod-Like Polymer Molecular Brush PBIEM254-g-P4MVP29 (L-rPMB). The reaction scheme to prepare rod-like PMB is shown in Scheme 2. Briefly, the inventors first synthesized poly(2-(bromoisobutyryloxy)ethyl methacrylate) (PBIEM) via reversible addition-fragmentation chain transfer (RAFT) polymerization.3 We then used the PBIEM backbone as a macro-initiator to graft P4MVP branches in a similar way as discussed in the preparation of the spherical PMB, and used GPC, NMR, and FTIR spectroscopy together with brush cleavage experiments to determine the brush size, graft density, and the degree of quaternization.

Figure 13A:
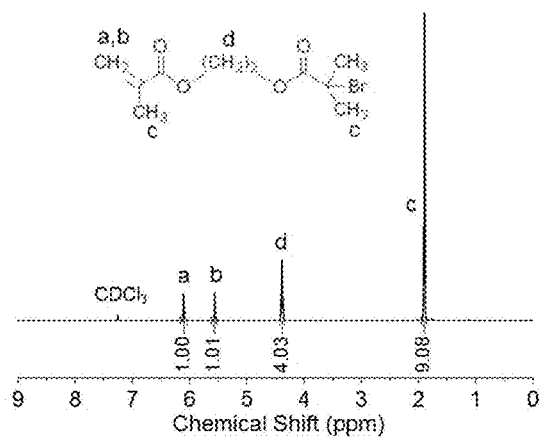
FIGS. 13A to 13F show the successful synthesis of the long rod-like L-rPMB, PBIEM$_{254}$-g-P4MVP$_{29}$.
Figure 13B:
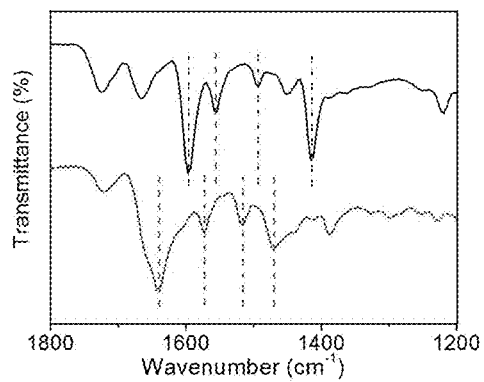
Figure 13C:
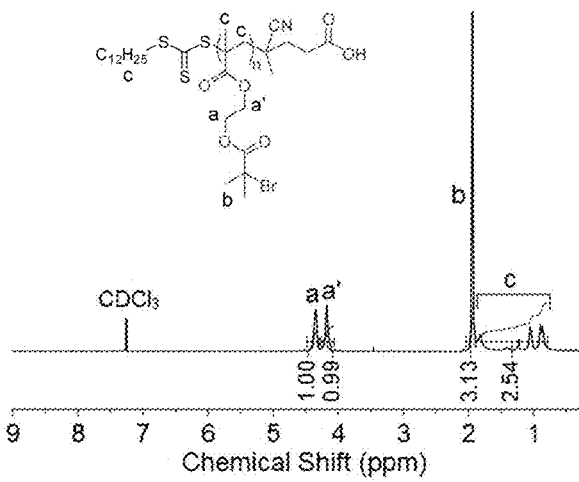
Figure 13D:
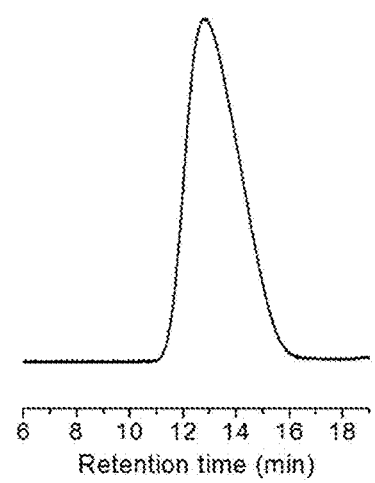

The 2-(bromoisobutyryloxy)ethyl methacrylate (BIEM, 2b) monomer was synthesized using a modified method following a previous report.[4] In a typical run, HEMA (5.0 g, 0.038 mol) and triethylamine (7.8 g, 0.077 mol) were dissolved in dichloromethane (48.9 g, 0.6 mol) in a round-bottomed Schlenk flask under nitrogen. The reaction mixture was stirred at 0° C. and degassed by N$_2$ for 45 min. α-bromoisobutyryl bromide (10.6 g, 0.046 mol) was then added drop-wise over a period of 20 min. After the reaction mixture was stirred for another 6 h at 0° C., the insoluble solids were filtered off. The filtrate was washed three times each with de-ionized water (3×50 mL), 0.5 M NaHCO$_3$ (3×50 mL) and saturated NaCl (3×50 mL) aqueous solutions, respectively. Subsequently, MgSO$_4$ was added to remove trace water and filtered off. The filtrate was evaporated to dryness. The final product, BIEM (2b), was further dried in a vacuum oven and its structure was confirmed by $^1$H NMR (FIG. 13A).

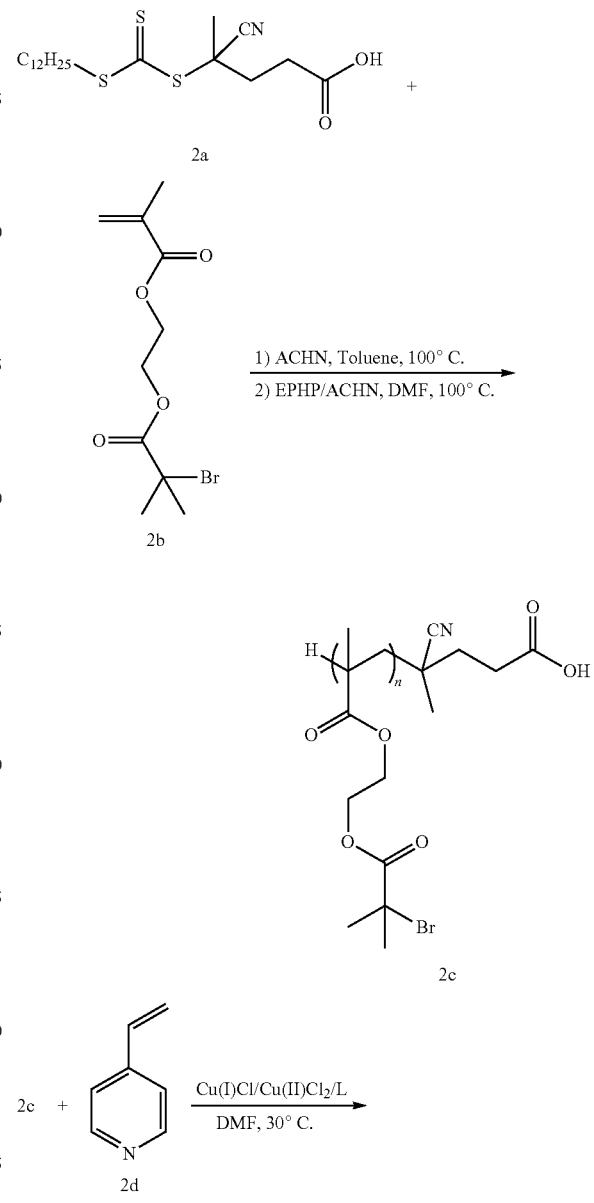

Figure 9:
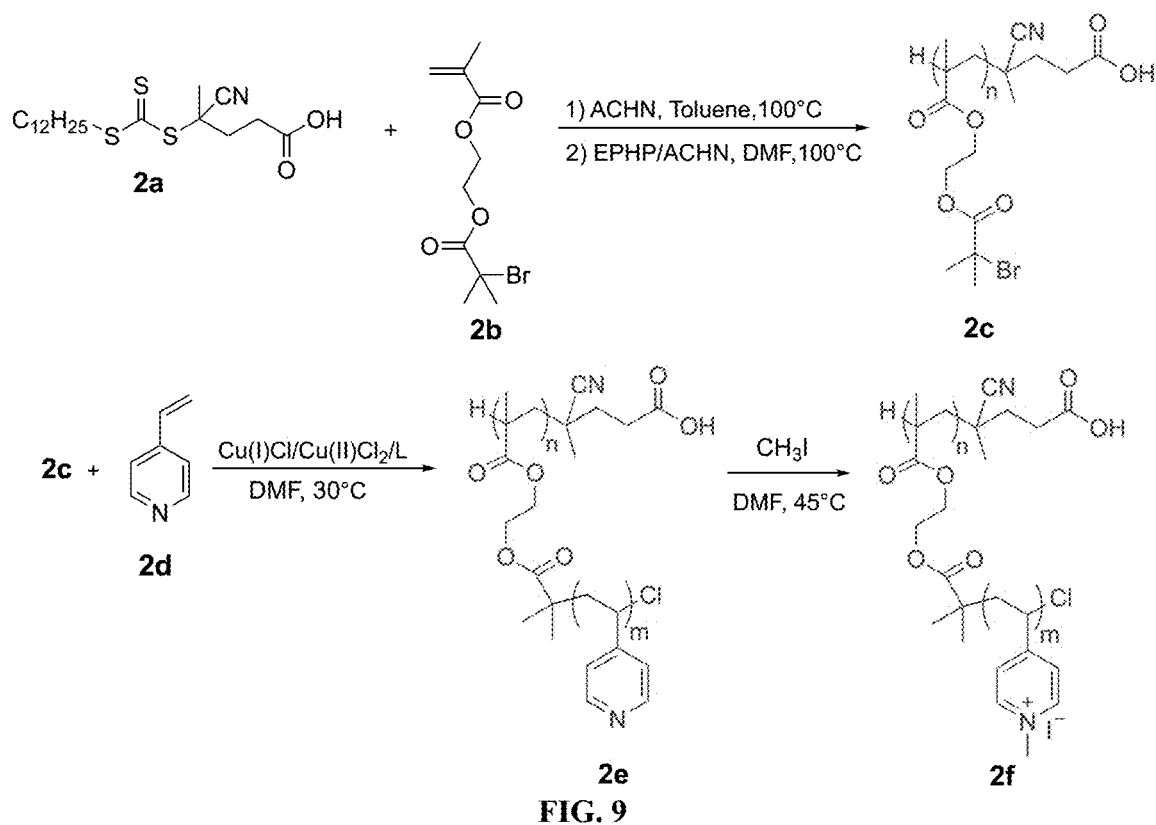
FIG. 9 shows chemical scheme S2. The reaction scheme to synthesize rod-like PMB, PBIEM-g-P4MVP.

FIG. 9, Scheme 12. The reaction scheme to synthesize rod-like PMB, PBIEM-g-P4MVP.

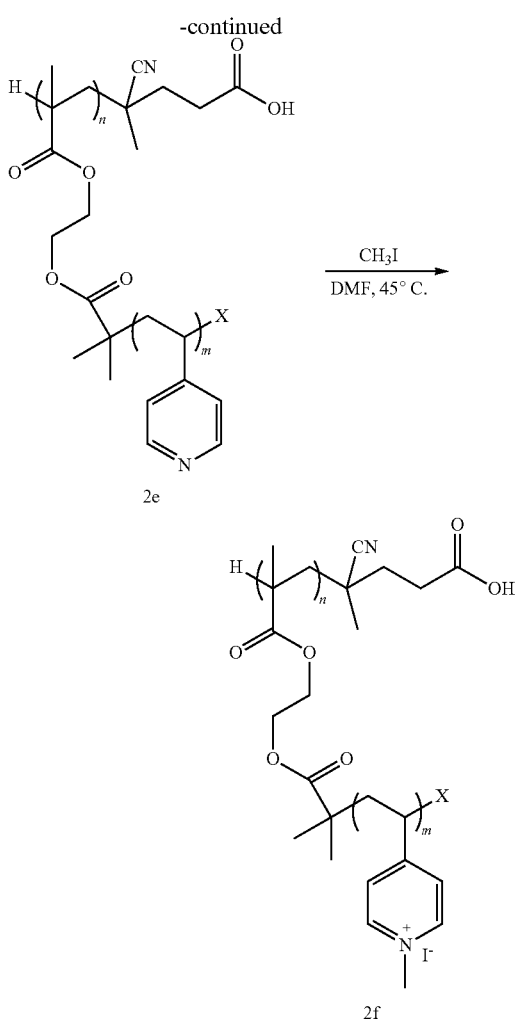

The backbone PBIEM (2c) was synthesized using RAFT polymerization with CDTSPA (2a) as the chain transfer agent. In a typical run, a mixture of BIEM (558 mg, 2.0 mmol), CDTSPA (2 mg, 5.0 μmol), ACHN (0.12 mg, 0.5 μmol) and toluene (2 mL) was placed in a 10 mL Schlenk flask equipped with a magnetic stir bar. After degassed by three freeze-pump-thaw cycles, the flask was sealed and immersed in a constant temperature bath at 100° C. After a predetermined time, the reaction mixture was diluted with toluene and precipitated in 10-fold methanol. After the product was collected by centrifugation and dried in a vacuum oven, a reduction step was performed using 1-ethylpiperidine hypophosphite (EPHP) to remove the trithiocarbonate moieties to obtain product 2c.[5-6]

After confirming the successful synthesis of $PBIEM_{254}$ with $^1H$ NMR and GPC (FIGS. 13C-D), we used the PBIEM as an ATRP macroinitiator, to synthesize the rod-like PMB, PBIEM-g-P4VP (2e). In a typical run, a mixture of $PBIEM_{254}$ (56.2 mg, 0.20 mmol initiating sites), $CuCl_2$ (13.5 mg, 0.10 mmol), $Me_6TREN$ (23.0 mg, 0.10 mmol), 4VP (4.2 g, 40 mmol, 2d), and DMF (6.0 g) was placed in a 25-mL Schlenk flask equipped with a magnetic stir bar. After degassed by three freeze-pump-thaw cycles, a mixture of CuCl (9.9 mg, 0.10 mmol), $Me_6TREN$ (23.0 mg, 0.10 mmol) and DMF (2.4 g) was injected to the solution under a nitrogen flow. The flask was sealed after three more freeze-pump-thaw cycles and immersed in a constant temperature bath at 30° C. for 3 h. The polymer product was collected by precipitating in 10-fold acetone and then reacted with excess iodomethane in DMF at 45° C. for 2 days to give the hydrophilic and cationic L-rPMB, $PBIEM_{254}$-g-$P4MVP_{29}$ (2F). After that the reaction mixture was precipitated in 10-fold diethyl ether. The final product was collected by centrifugation and dried in a vacuum oven overnight.

Besides characterizing the successful synthesis of products 2b through 2f using $^1H$ NMR, GPC and FTIR spectra, the inventors also characterized the size of individual P4VP branches by cleaving them from the PBIEM backbone. In a typical cleavage experiment, 30 mg of the rod-like PMB, $PBIEM_{254}$-g-$P4MVP_{29}$, was dissolved in 3 mL of DMF and mixed with 0.5 mL of 5 M KOH (in methanol) solution. The mixture was sealed and heated at 60° C. for 48 h. The resultant crude products were poured into 100 mL of dichloromethane and washed with saturated saline aqueous solution for 5 times. $MgSO_4$ was added to remove trace water and filtered off afterward. The filtrate was precipitated in diethyl ether for three times and dried in a vacuum oven.

Characterization Results. The monomer BIEM (2b) was prepared via a one-step nucleophilic substitution reaction between a monomer HEMA and α-bromoisobutyryl bromide. The successful synthesis was confirmed by $^1H$ NMR spectrum (FIG. 13A): δ=6.10 and 5.56 ppm (peak a, b, $CH_2$=C), δ=4.40 ppm (peak d, $CH_2$—O), δ=1.87~1.94 ppm (peak c, $CH_3$).

The linear polymer backbone (PBIEM, 2c) was synthesized via RAFT polymerization. The successful polymerization was confirmed by $^1H$ NMR (FIG. 13C), showing the chemical shifts of two characteristic methylene protons adjacent to oxygen moieties located at δ=4.38 and 4.20 ppm (peak a and a'). Because of the large size of PBIEM we prepared, we did not use $^1H$ NMR to estimate its molecular weight. The molecular weight ($M_n$) and molecular weight distribution of PBIEM were revealed by GPC analysis (FIG. 13D): GPC reports a $M_n$ of 71 kDa (i.e. DP=254) and a PDI of 1.25.

Figure 13E:
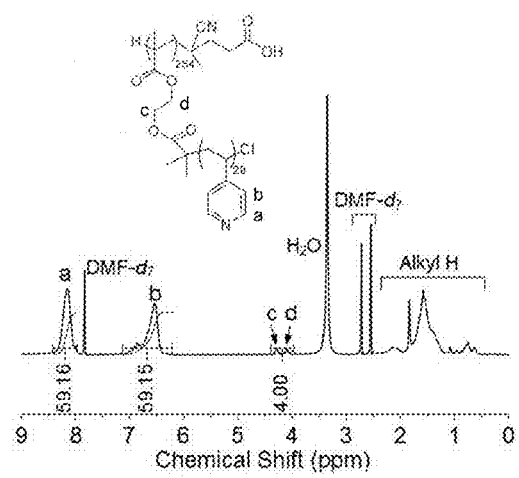
Figure 13F:
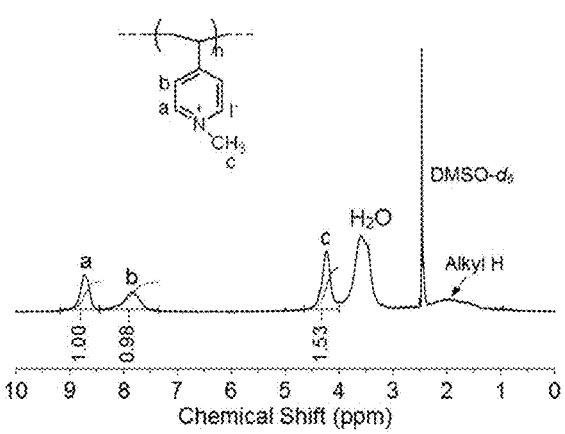

The inventors used ATRP to synthesize well-defined rod-like PMB, PBIEM-g-P4VP (2e), at relatively low monomer conversions (<15%), which helps reduce possible intermolecular coupling between alkyl chloride chain ends and the pyridine units. The successful synthesis of $PBIEM_{254}$-g-$P4VP_{29}$ was confirmed by $^1H$ NMR (FIG. 13E). The size of P4VP branches was determined by comparing the integral areas of protons on the pyridine rings of P4VP branches (peak a or b) with that of methylene protons adjacent to oxygen moieties of the PBIEM backbone (peak c and d), assuming 100% graft density, i.e. each ATRP initiator site on individual BIEM repeating units initiated the polymerization of a P4VP branch similar to what was found in the synthesis of spherical PMB. Our analysis shows that each P4VP branch contains ~29 units. The analysis of reaction conversion suggested a DP of 30. The DPs determined by $^1H$ NMR analysis and reaction conversion agree with each other.

The rod-like PMB $PBIEM_{254}$-g-$P4VP_{29}$ was subsequently converted to its hydrophilic and cationic form L-rPMB, i.e. $PBIEM_{254}$-g-$P4MVP_{29}$, via a quaternization reaction, and the successful synthesis was confirmed by $^1H$ NMR (FIG. 13F) and FTIR (FIG. 13B) spectra. In $^1H$ NMR, the two characteristic peaks of the protons of the pyridine moieties of 4-VP units (a and b in FIG. 13E) shift completely to higher positions (a and b in FIG. 13F) after quaternization. In FTIR (FIG. 13B), the main characteristic peaks of the pyridine moieties of 4-VP units (labeled with green dotted lines) also shifted completely to higher wavenumbers (labeled with pink dotted lines) after the quaternization.

Figure 14:
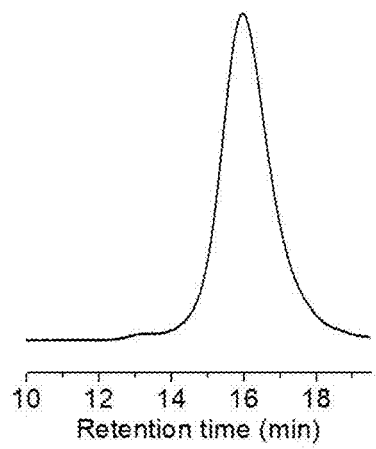
FIG. 14 shows GPC of individual P4VP branches cleaved from the long rod-like L-rPMB before its quaternization suggests a P4VP graft density of 88%.

Finally, the inventors characterized individual P4VP branches cleaved from the PBIEM backbone in a similar way as described earlier to further confirm the successful synthesis of the well-defined rod like PMB and estimate the graft density. As an example, the GPC (FIG. 14) reports a molecular weight ($M_n$) of 3,500 Da and a PDI of 1.23, respectively, of the cleaved P4VP branches. The inventors estimated the graft density of P4VP branches on the rod-like PMB by comparing the molecular weight of the P4VP branches determined by NMR (FIG. 13E) with that of the cleaved P4VP branches reported by GPC (FIG. 14). Here the graft density is defined as the percentage of individual BIEM repeating units that successfully initiated the growth of a P4VP branch. Our estimation suggests a P4VP$_{29}$ graft density of ~88% on the long rod-like PMB.

Synthesis of Well-Defined Short Rod-Like Polymer Molecular Brush PBIEM$_{64}$-g-P4MVP$_{31}$ (S-rPMB). A shorter rod-like PMB, PBIEM$_{64}$-g-P4MVP$_{31}$, was synthesized in a similar way as PBIEM$_{254}$-g-P4MVP$_{29}$. PBIEM$_{64}$ was first synthesized using RAFT polymerization with CDT-SPA (2a) as the chain transfer agent. In a typical run, a mixture of BIEM (800 mg, 2.86 mmol), CDTSPA (11.6 mg, 28.7 µmol), ACHN (0.8 mg, 4 µmol) and toluene (2 mL) was placed in a 10 mL Schlenk flask equipped with a magnetic stir bar. After degassed by three freeze-pump-thaw cycles, the flask was sealed and immersed in a constant temperature bath at 100° C. After a predetermined time, the reaction mixture was diluted with toluene and precipitated in 10-fold hexanes. After the product was collected by centrifugation and dried in a vacuum oven, a reduction reaction was performed using EPHP to remove the trithiocarbonate moieties to obtain the PBIEM product (2c).

After confirming the successful synthesis of PBIEM$_{64}$ with $^1$H NMR and GPC (FIGS. 15A, 15B), the inventors used it as the ATRP macroinitiator to synthesize the rod-like PMB. In a typical run, a mixture of PBIEM (25.0 mg, 89.6 µmol initiating sites), CuCl$_2$ (5.8 mg, 43.1 µmol), Me$_6$TREN (10.0 mg, 43.4 µmol), 4VP (1.50 g, 14.3 mmol), and DMF (2.5 g) was placed in a 10 mL Schlenk flask equipped with a magnetic stir bar. After degassed by three freeze-pump-thaw cycles, a mixture of CuCl (4.4 mg, 44.4 µmol), Me$_6$TREN (10.0 mg, 43.4 µmol) and DMF (1.0 g) was injected to the solution under a nitrogen flow. The flask was sealed after three more freeze-pump-thaw cycles and immersed in a constant temperature bath at 30° C. for 6.5 h. The polymer product was collected by first precipitating in acetone, followed by ethyl ether. After dried in vacuum, the polymer was reacted with excess iodomethane in DMF at 45° C. for 1 day to give the hydrophilic and cationic S-rPMB, i.e. PBIEM$_{64}$-g-P4MVP$_{31}$. The final product was precipitated in 10-fold diethyl ether and dried in a vacuum oven overnight.

Characterization Results. The successful synthesis of PBIEM$_{64}$ was confirmed by $^1$H NMR (FIG. 15A), which shows the chemical shifts of two characteristic methylene protons adjacent to oxygen moieties located at 4.38, 4.20 ppm (peak a and a'). The degree of polymerization (DP=64) was estimated by comparing the number of protons at 4.38 and 4.20 ppm with those at 3.23 or 1.24 ppm. The molecular weight ($M_n$) and molecular weight distribution of PBIEM$_{64}$ were further characterized by GPC (FIG. 15B): GPC reports a $M_n$ of 20 kDa (i.e. DP=70) with a small PDI of 1.14, in good agreement with the NMR result.

The successful synthesis of PBIEM$_{64}$-g-P4VP$_{31}$ was confirmed by $^1$H NMR (FIG. 15C). The size of P4VP branches was determined by comparing the integral areas of protons on the pyridine rings on P4VP branches (peak a or b) with that of methylene protons adjacent to oxygen moieties of the PBIEM backbone (peak c and d), assuming 100% graft density. Our analysis shows that each P4VP branch contains ~31 units. The analysis of reaction conversion suggested a DP of 30. The DPs determined by $^1$H NMR analysis and reaction conversion agree well with each other.

The rod-like PMB, PBIEM$_{64}$-g-P4VP$_{31}$, was subsequently converted to its hydrophilic and cationic form PBIEM$_{64}$-g-P4MVP$_{31}$ via a quaternization reaction, and the successful synthesis was confirmed by $^1$H NMR (FIG. 15D): the two characteristic peaks of the protons of the pyridine moieties of 4-VP units (a and b in FIG. 15C) shifted completely to higher positions (a and b in FIG. 15D) after the quaternization, and a new peak from N-methyl group was shown at 4.27 ppm. The ratio of protons from pyridine ring to those from N-methyl group was 4:3, indicating a 100% quaternization.

Synthesis of Well-Defined P4VP$_{28}$ Control Quaternized by Alkyl Iodide with Different Alkyl Chain Length. Besides obtaining individual P4VP branches by cleaving them directly from their respective PMBs, we also prepared well-defined P4VP$_{28}$ via RAFT polymerization (Scheme 3). In a typical run, a mixture of 4VP (2.1 g, 20 mmol), S-1-dodecyl-S'-(α,α'-dimethyl-α''-acetic acid) trithiocarbonate (145 mg, 0.4 mmol), AIBN (8.4 mg, 0.05 mmol) and THF (2.0 mL) was placed in a 10 mL Schlenk flask. After degassed by three freeze-thaw cycles, the flask was sealed and stirred in a temperature controlled oil bath kept at 60° C. for a prescribed amount of time. After the heating was stopped, the reaction mixture was diluted with THF and then precipitated in 10-fold petroleum ether. The product was collected by centrifugation and dried in a vacuum oven at room temperature.

Figure 10:
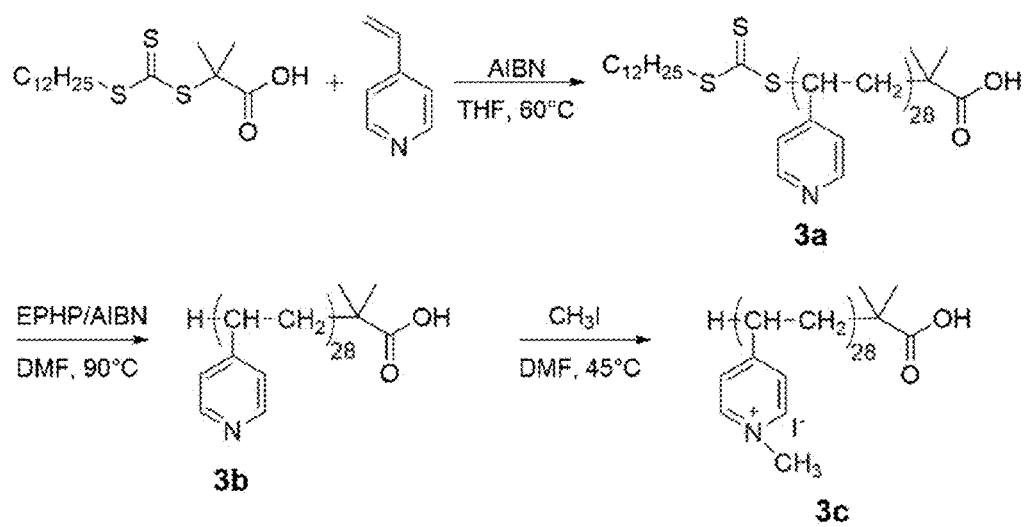
FIG. 10 shows chemical scheme S3. The reaction scheme to synthesize P4MVP$_{28}$ via RAFT polymerization.

FIG. 10, Scheme 13. The reaction scheme to synthesize P4MVP$_{28}$ via RAFT polymerization.

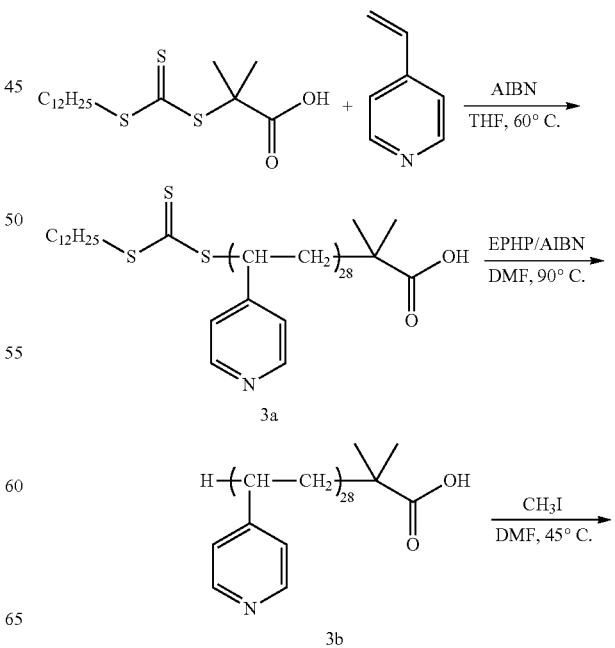

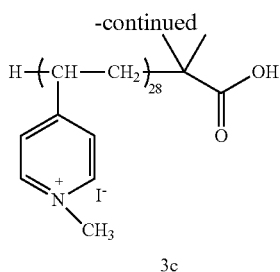

3c

After confirming the successful synthesis of P4VP$_{28}$ (3a), a reduction step was performed using EPHP to remove the trithiocarbonate moieties to obtain product 3b$^5$. UV-Vis and $^1$H NMR experiments were used to confirm the successful removal. The product was then reacted with excess iodomethane in DMF at 45° C. for 2 days to give the hydrophilic and cationic P4MVP$_{28}$ (3c). The reaction mixture was finally precipitated in 10-fold diethyl ether. The final product was collected by centrifugation and dried in a vacuum oven overnight.

The inventors also quaternized P4VP$_{28}$ with alkyl iodides of different alkyl chain length in a similar way to obtain P4EVP$_{28}$ (i.e. quaternized with ethyl iodide), P4BVP$_{28}$ (i.e. quaternized with butyl iodide), P4HVP$_{28}$ (i.e. quaternized with hexyl iodide), P4OVP$_{28}$ (i.e. quaternized with octyl iodide), and P4DVP$_{28}$ (i.e. quaternized with dodecyl iodide).

Characterization Results. After the linear P4VP$_{28}$ (3a) was synthesized via RAFT polymerization, we used a combination of characterization methods such as $^1$H NMR, GPC, and reaction conversion analysis to confirm the successful synthesis and determine the DP. DPs determined by different methods agreed with each other.

In $^1$H NMR spectrum (FIG. 16A), a DP of 28 was determined by comparing the integral areas of protons on pyridine rings of P4VP (peak a or b) with that of methylene protons adjacent to sulfur atom of trithiocarbonate moieties (peak c). Our analysis of reaction conversion also suggested a DP of 28. We further used GPC (FIG. 16B) to reveal a molecular weight ($M_n$) of 3050 Da and a narrow molecular weight distribution, with a PDI of 1.15. These data confirmed the successful synthesis of well-defined P4VP$_{28}$.

After removing the trithiocarbonate moiety using EPHP,$^5$ the P4VP$_{28}$ was subsequently converted to its hydrophilic and cationic form P4MVP$_{28}$ (3c) via a quaternization reaction, and the successful synthesis was confirmed by $^1$H NMR (FIG. 16C): the two characteristic peaks of the protons on 4VP (a and b in FIG. 16A) move completely to their higher chemical shifts (a in b in FIG. 16C) after the 100% quaternization. We confirmed the successful synthesis of P4EVP$_{28}$, P4BVP$_{28}$, P4HVP$_{28}$, P4OVP$_{28}$, and P4DVP$_{28}$, respectively, in a similar way (data not shown).

FIGS. 11A to 11E show the successful synthesis of the spherical sPMB, β-CD-g-P4MVP$_{28}$. The structure of ATRP macroinitiator Br-β-CD is confirmed by $^1$H NMR (FIG. 11A, CDCl$_3$ as solvent), and FTIR spectra (FIG. 11A) (red trace; compared to that of the β-CD, black trace). NMR analysis shows that 89.4% of the 21-OH groups on the β-CD core are substituted with α-bromoisobutyryl groups. We confirmed the successful synthesis of spherical PMB β-CD-g-P4VP$_{28}$ (FIG. 11C, in DMF-d$_7$) and the sPMB β-CD-g-P4MVP$_{28}$ (FIG. 11D, in DMSO-d$_6$) by $^1$H NMR analysis, as well as the FTIR spectra (FIG. 11E) of the sPMB before (black) and after (red) 100% quaternization of its P4VP branches.

FIGS. 12A to 12B show Brush cleavage experiment reveals a P4VP graft density of 90% on the spherical sPMB. (FIG. 12A) $^1$H NMR spectrum of the cleaved P4VP branches from the spherical PMB, β-CD-g-P4VP$_{28}$. An analysis of the integrated peak areas suggests that the P4VP branches have a DP=31; (FIG. 12B) GPC trace of P4VP branches cleaved from the spherical PMB β-CD-g-P4VP$_{28}$ reports a DP of 29 and a PDI of 1.19, agreeing well with the P4VP sizes derived from NMR analysis. By comparing the size of the cleaved P4VP branches derived from NMR analysis to that of the P4VP branches in the spherical PMB (also derived from NMR analysis), the P4VP graft density is calculated as ~90%. This value is very close to the graft density of α-bromoisobutyryl groups on the β-CD core (FIGS. 11A-E), suggesting that every α-bromoisobutyryl group initiated the successful growth of a P4VP branch.

FIGS. 13A to 13E show the successful synthesis of the long rod-like L-rPMB, PBIEM$_{254}$-g-P4MVP$_{29}$. (FIG. 13A) $^1$H NMR spectrum confirms successful synthesis of BIEM (CDCl$_3$ as solvent); (FIG. 13B) FTIR spectra of PBIEM$_{254}$-g-P4VP$_{29}$ before (black) and after 100% quaternization of the P4VP branches (red trace); (FIG. 13C) $^1$H NMR spectrum and (FIG. 13D) GPC trace of the PBIEM$_{254}$ backbone ($M_n$=71.0 kDa, PDI=1.25). The successful synthesis of the long rod-like PMB, PBIEM$_{254}$-g-P4VP$_{29}$ is confirmed by $^1$H NMR spectra of the PMB before (FIG. 13E, in DMF-d$_7$) and after (f, in DMSO-d$_6$) 100% quaternization of the P4VP branches.

FIG. 14 shows GPC of individual P4VP branches cleaved from the long rod-like L-rPMB before its quaternization suggests a P4VP graft density of 88%. GPC trace of P4VP branches cleaved from the rod-like PBIEM$_{254}$-g-P4VP$_{29}$ reports a DP of 33 and a PDI of 1.23. This DP is slightly larger than that of the P4VP branches in the PMB (i.e., DP=29), suggesting a graft density of ~88%.

FIGS. 15A to 15D, FIG. 15. Successful synthesis of the short rod-like S-rPMB, PBIEM$_{64}$-g-P4MVP$_{31}$. (FIG. 15A) $^1$H NMR spectrum (in CDCl$_3$) and (FIG. 15B) GPC trace of the PBIEM$_{64}$ backbone ($M_n$=20 kDa, PDI=1.14). The Successful synthesis of the short rod-like PMB, PBIEM$_{64}$-g-P4VP$_{31}$ is confirmed by $^1$H NMR spectra of the PMB before (FIG. 15C, in DMF-d$_7$) and after (FIG. 15D, in DMF-d$_7$) 100% quaternization of the P4VP branches.

FIG. 16A to 16C, FIG. 16. The linear-chain P4MVP$_{28}$ control prepared via RAFT polymerization. (FIG. 16A) $^1$H NMR spectrum of the as-synthesized P4VP$_{28}$. The DP was calculated based on peak integration analysis; (FIG. 16B) GPC spectrum of the as-synthesized P4VP$_{28}$ ($M_n$=3,050 Da, PDI=1.15). The polymer size measured by GPC agrees well with that derived from the NMR analysis; (FIG. 16C) $^1$H NMR spectrum of the P4VP$_{28}$ control after removing the trithiocarbonate moiety and 100% quaternization.

Figure 17A:
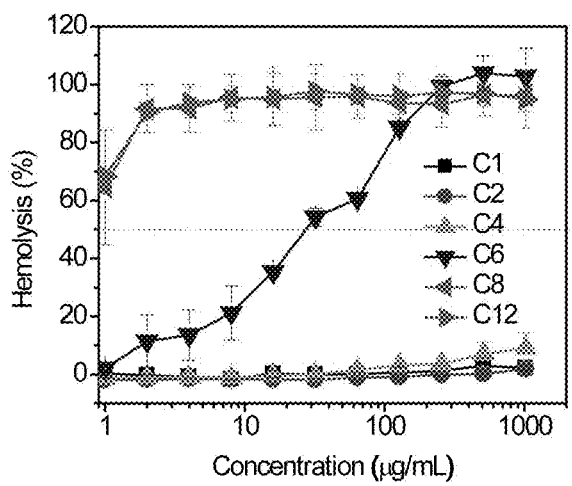
FIGS. 17A and 17B show biological assays of P4VP$_{28}$ quaternized by alkyl iodides of different alkyl chain length illustrate the dilemma of walking a fine line between the cationic-hydrophobic boundary in the hope of trading toxicity with antimicrobial activity.
Figure 17B:
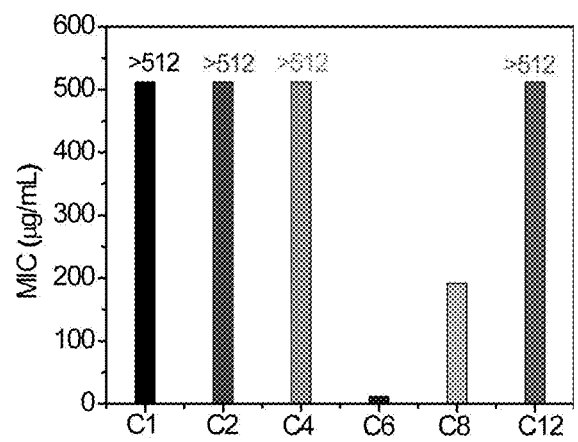

FIGS. 17A and 17B show the results from biological assays of P4VP$_{28}$ quaternized by alkyl iodides of different alkyl chain length illustrate the dilemma of walking a fine line between the cationic-hydrophobic boundary in the hope of trading toxicity with antimicrobial activity.

FIG. 17A shows hemolysis assays over HRBCs show that when the alkyl chain length is between C1 to C4 (i.e. from methyl iodide to butyl iodide), the quaternized P4VP$_{28}$ is non-hemolytic; when the alkyl chain length increases to C6 and above, the quaternized P4VP$_{28}$ becomes highly hemolytic; FIG. 17B shows the minimum inhibitory concentration (MIC) assays against E. coli demonstrate that the hemocompatible P4VP$_{28}$ quaternized by alkyl iodides with alkyl chain length from C1 to C4 has very low antimicrobial activity; the most antimicrobial active candidate is P4HVP$_{28}$ (i.e. alkyl chain length C6), which presumably has the hydrophobic-cationic "balance" to gain desirable antimicrobial activity, but is unfortunately quite toxic and causes serious hemolysis (see C6 trace in FIG. 17A).

FIG. 18 shows a comparison of the hemagglutination activity between nanostructured PMBs and linear-chain P4MVP$_{28}$. The concentration of all polymers was set as 512 µg/mL. Although both the nanostructured PMBs and linear-chain P4MVP$_{28}$ are non-hemolytic, the linear-chain P4MVP$_{28}$ is a strong blood coagulation agent while the nanostructured PMBs cause little hemagglutination.

FIGS. 19A to 19L show confocal microscopy shows no dye leakage from mammalian cell-mimicking GUVs when interacting with PMBs and P4MVP$_{28}$ (scale bar: 50 µm). The polymers are adsorbed spontaneously on the GUV surface, as exemplary confocal pictures reveal L-rPMB (19A, blue, labeled with Alexa-647), individual mammalian cell-mimicking GUVs (19B, red, labeled with rhodamine), and their co-localization (19C). Exemplary time-lapse confocal pictures of the mammalian cell-mimicking GUVs (red, labeled with rhodamine) loaded with fluorescein (green) when interacting with P4MVP$_{28}$ (19D-19F), the L-rPMB (19G-19I) and sPMB (19J-19L) for different times (19D, 19G, 19J: 0 sec; 19E, 19H, 19K: 240 sec; 19F, 19I, 19L: 420 sec) demonstrate that neither the nanostructured PMBs nor the linear-chain P4MVP$_{28}$ rupture the mammalian cell-mimicking GUVs.

FIGS. 20A to 20L show confocal microscopy shows selective dye leakage from *E. coli*-mimicking GUVs when interacting with nanostructured PMBs but not with the linear-chain P4MVP$_{28}$ (scale bar: 50 µm). The polymers are adsorbed spontaneously on the GUV surface, as exemplary confocal pictures reveal P4MVP$_{28}$ (20A, blue, labeled with Alexa-647), individual *E. coli*-mimicking GUVs (20B, red, labeled with rhodamine), and their co-localization (20C). Exemplary time-lapse confocal pictures of the *E. coli*-mimicking GUVs (red, labeled with rhodamine) loaded with fluorescein (green) when interacting with P4MVP$_{28}$ (20D-20F), the L-rPMB (20G-20I) and sPMB (20J-20L) for different times (20D, 20G, 20J: 0 sec; 20E, 20H, 20K: 240 sec; 20F, 20I, 20L: 420 sec) demonstrate that the nanostructured PMBs rupture the *E. coli*-mimicking GUV membranes and cause dye release, while the linear-chain P4MVP$_{28}$ does not do that.

Figure 21A:
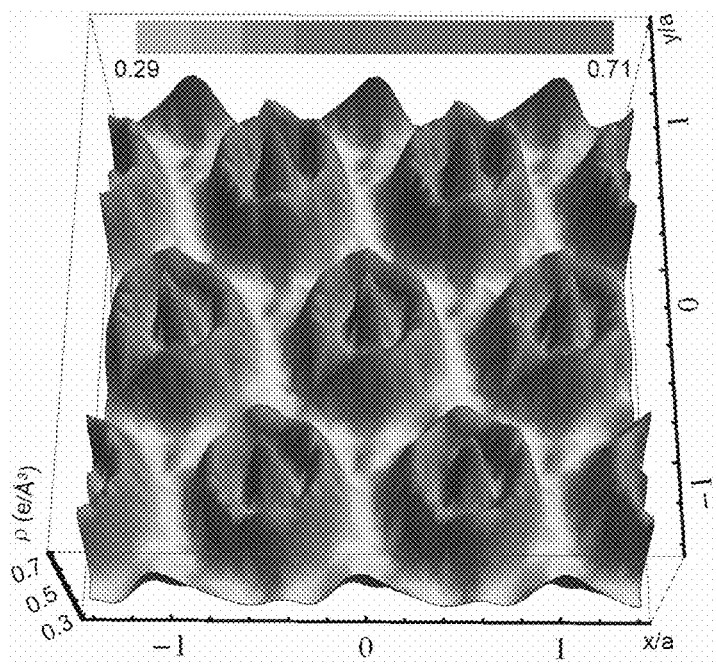
FIGS. 21A and 21B shows that hydrophilic and nanostructured PMBs remodel bacterial membranes by inducing a topological transition to form membrane pores.
Figure 21B:
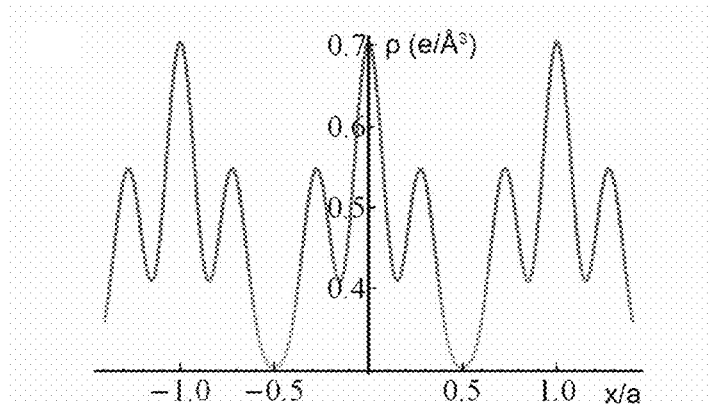

FIGS. 21A and 21B shows the hydrophilic and nanostructured PMBs remodel bacterial membranes by inducing a topological transition to form membrane pores. (FIG. 21A) Fourier reconstructed 3D electron density map of *E. coli*-mimicking membranes incubated with sPMB reveals the formation of 2D hexagonally packed pores. The color scale bar of electron density (ρ) is shown at the top, and x/a, y/a represent perpendicular axes along the membrane plane normalized by the lattice parameter. (FIG. 21B) The 1D electron density profile along the unit cell x-axis further confirms that each sPMB (p=0.71 e/Å$^3$) sits in the center of individual pores and is surrounded by a rim (p=0.55 e/Å$^3$) of lipid headgroups that are closely associated with the P4MVP branches of each PMB, and the pores organize themselves into an inverted 2D hexagonal membrane phase (H$_{II}$).

Figures 22A, 22B, 22C:
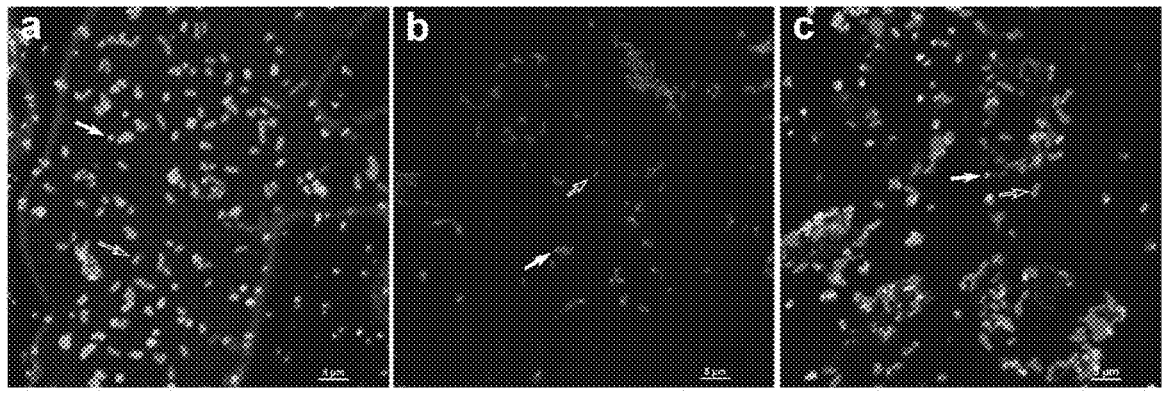
FIGS. 22A to 22C shows the nanostructure-dependent antimicrobial selectivity of PMBs directly visualized under confocal microscope using the bacteria live/dead assay.

FIGS. 22A to 22C show the nanostructure-dependent antimicrobial selectivity of PMBs directly visualized under confocal microscope using the bacteria live/dead assay. A bacteria mixture comprised of cylinder-shaped *E. coli* (labelled by black arrow as an example) and spherical *S. aureus* (labelled by white arrow as an example) are stained by DMAO and EthD-III. Bacteria with intact cell membranes (i.e. live) stain fluorescent green, whereas bacteria with damaged cell membranes (i.e. dead) stain fluorescent red. (FIG. 22A) The control sample of bacteria mixture without PMBs. Nearly all bacteria cells stain fluorescent green, with only a couple of naturally existing dead *E. coli* and *S. aureus* cells that stain fluorescent red. (FIG. 22B) Bacteria mixture incubated with sPMB. All bacteria cells from both bacterial families are dead and stain fluorescent red. (FIG. 22C) Bacteria mixture incubated with L-rPMB. Nearly all *E. coli* cells are dead and stain fluorescent red. The remaining live cells that stain fluorescent green are nearly all *S. aureus*. This assay clearly demonstrates that while sPMB kills both bacteria, L-rPMB selectively kill Gram− *E. coli* in the presence of Gram+ *S. aureus*.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Lee, M. W.; Han, M.; Bossa, G. V.; Snell, C.; Song, Z. Y.; Tang, H. Y.; Yin, L. C.; Cheng, J. J.; May, S.; Luijten, E.; Wong, G. C. L., Interactions between membranes and "metaphilic" polypeptide architectures with diverse side-chain populations. *ACS Nano* 2017, 11 (3), 2858-2871.

Hu, K.; Schmidt, N. W.; Zhu, R.; Jiang, Y. J.; Lai, G. H.; Wei, G.; Palermo, E. F.; Kuroda, K.; Wong, G. C. L.; Yang, L. H., A critical evaluation of random copolymer mimesis of homogeneous antimicrobial peptides. *Macromolecules* 2013, 46 (5), 1908-1915.

Chakraborty, S.; Liu, R. H.; Hayouka, Z.; Chen, X. Y.; Ehrhardt, J.; Lu, Q.; Burke, E.; Yan, Y. Q.; Weisblum, B.; Wong, G. C. L.; Masters, K. S.; Gellman, S. H., Ternary Nylon-3 copolymers as host-defense peptide mimics: Beyond hydrophobic and cationic subunits. *J. Am. Chem. Soc.* 2014, 136 (41), 14530-14535.

SYNTHESIS REFERENCES

1. Patten, T. E.; Matyjaszewski, K., Atom transfer radical polymerization and the synthesis of polymeric materials. *Adv. Mater.* 1998, 10 (12), 901-915. DOI: 10.1002/(SICI) 1521-4095 (199808)10:12<901:AID-ADMA901>3.3.CO; 2-2.

2. Kuang, L. J.; Fernandes, D. A.; O'Halloran, M.; Zheng, W.; Jiang, Y. J.; Ladizhansky, V.; Brown, L. S.; Liang, H. J., "Frozen" block copolymer nanomembranes with light-driven proton pumping performance. *ACS Nano* 2014, 8 (1), 537-545. DOI: 10.1021/nn4059852.

3. Moad, G.; Rizzardo, E.; Thang, S. H., Living radical polymerization by the RAFT process. *Aust. J. Chem.* 2005, 58 (6), 379-410. DOI: 10.1071/CH05072.

4. Venkatesh, R.; Yajjou, L.; Koning, C. E.; Klumperman, B., Novel brush copolymers via controlled radical polymerization. *Macromol. Chem. Phys.* 2004, 205 (16), 2161-2168. DOI: 10.1002/macp.200400252.

5. Chong, Y. K.; Moad, G.; Rizzardo, E.; Thang, S. H., Thiocarbonylthio end group removal from RAFT-synthesized polymers by radical-induced reduction. *Macromolecules* 2007, 40 (13), 4446-4455. DOI: Doi 10.1021/Ma062919u.

6. Moad, G.; Chong, Y. K.; Postma, A.; Rizzardo, E.; Thang, S. H., Advances in RAFT polymerization: the synthesis of polymers with defined end-groups. *Polymer* 2005, 46 (19), 8458-8468. DOI: 10.1016/j.polymer.2004.12.061.

What is claimed is:

1. A method of making biodegradable spherical polymer molecular brushes (PMBs) with specific structures and high hydrophilicity via controlled polymerization methods comprising:

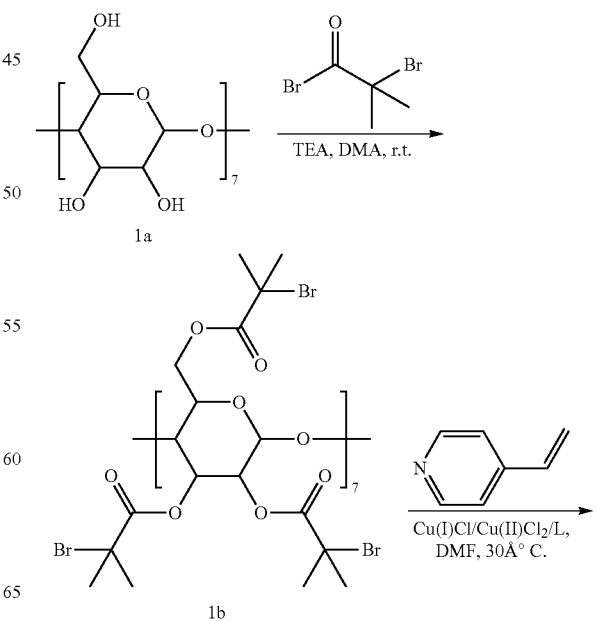

-continued

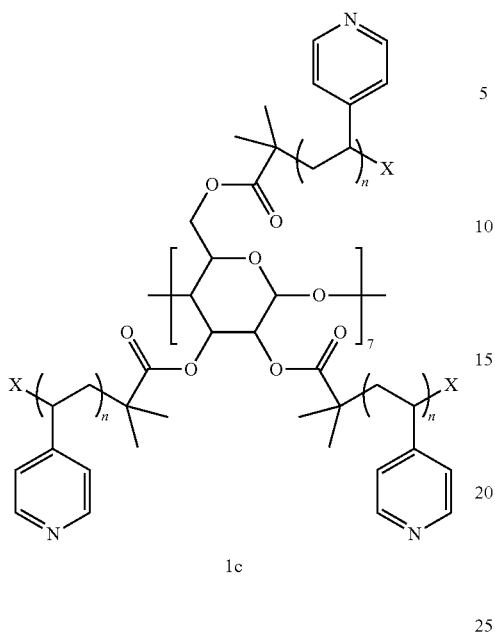

1c

-continued

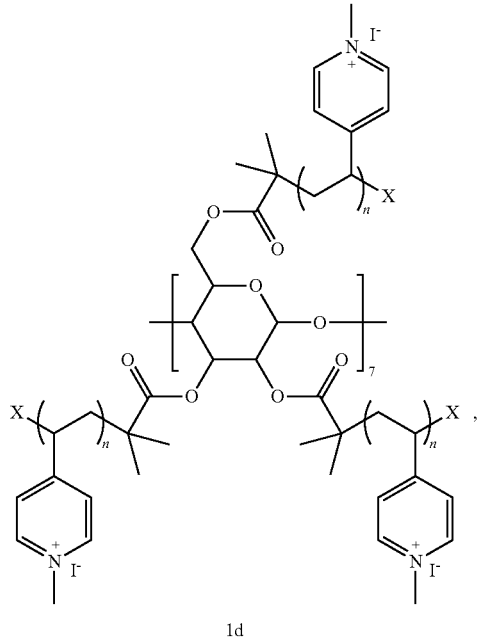

1d

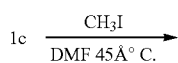

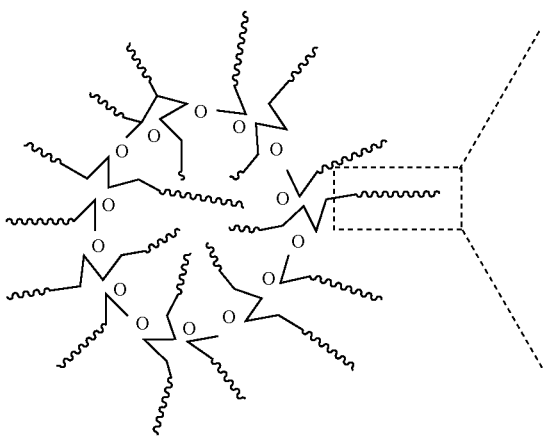

wherein the spherical backbone is a biodegradable polymer and the hydrophilic polymer brushes are poly(2-(trimethylamino)ethyl methacrylate) (PTMAEMA).

2. The method of claim 1, wherein the length n is 1 to 20, 20 to 40, 40 to 60, 60 to 80, 80 to 100, or more than 100.

3. The method of claim 1, wherein X is selected from Cl or Br.

4. The method of claim 1, wherein a spherical backbone is selected from at least one of sucroses, cyclodextrins, glycogens, phytoglycogen or other environmentally degradable molecules.

5. The method of claim 1, wherein the hydrophilic polymer brushes further comprise poly(4-vinyl-N methylpyridine iodide) (P4MVP), or other polyelectrolytes including polyester and polypeptides.

6. The method of claim 1, wherein the PMB at least one of: selectively disrupts bacterial membranes while not disrupting mammalian cell membranes, is environmentally degradable, has antimicrobial activity while in use in an animal but is dismantled into antimicrobially inactive pieces when released into a natural habitat, is a nanostructure that is either a nanorod or a nanosphere, or is formulated in a pharmaceutically acceptable carrier in an amount effective to reduce or eliminate a bacterial infection.

* * * * *